(12) United States Patent
Xu et al.

(10) Patent No.: US 10,308,573 B2
(45) Date of Patent: *Jun. 4, 2019

(54) PROCESS FOR MAXIMIZING XYLENES PRODUCTION FROM HEAVY AROMATICS FOR USE THEREIN

(71) Applicant: Saudi Arabian Oil Company, Dhahran (SA)

(72) Inventors: Qi Xu, Dhahran (SA); Raed Abudawoud, Khobar (SA); Ahmad A. Jazzar, Riyadh (SA); Zhonglin Zhang, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/018,394

(22) Filed: Jun. 26, 2018

(65) Prior Publication Data

US 2018/0339954 A1 Nov. 29, 2018

Related U.S. Application Data

(63) Continuation of application No. 15/606,600, filed on May 26, 2017, now Pat. No. 10,035,742.

(51) Int. Cl.
*C07C 15/08* (2006.01)
*C10G 45/46* (2006.01)
(Continued)

(52) U.S. Cl.
CPC .............. *C07C 15/08* (2013.01); *C07C 6/126* (2013.01); *C10G 45/44* (2013.01); *C10G 45/46* (2013.01);
(Continued)

(58) Field of Classification Search
CPC ........... C07C 15/08; C07C 1/20; C07C 15/06; C07C 15/04; C07C 2/66; C07C 4/18;
(Continued)

(56) References Cited

U.S. PATENT DOCUMENTS 4,013,734 A 3/1977 Kim
4,127,471 A 11/1978 Suggitt et al.
(Continued)

FOREIGN PATENT DOCUMENTS

EP 0816311 A1 1/1998
WO WO0010944 A1 3/2000
(Continued)

OTHER PUBLICATIONS

Commissaris, Scott E.; "UOP Parex Process", Handbook of Petroleum Refining Processes Third Edition, 2004, Chapter 2.6, pp. 2.47-2.53.
(Continued)

*Primary Examiner* — Sharon Pregler
(74) *Attorney, Agent, or Firm* — Bracewell LLP; Constance Gall Rhebergen

(57) ABSTRACT

A method for producing xylenes from a heavy reformate feed includes the steps of introducing the heavy reformate feed and a hydrogen feed to a dealkylation reactor, reacting the heavy reformate feed with the hydrogen gas in the presence of the dealkylation catalyst in the dealkylation reactor to produce a dealkylation effluent, introducing the dealkylation effluent to a splitter unit, separating the dealkylation effluent into a light gas stream, a toluene stream, a benzene stream, a C9 aromatics stream, a C10+ aromatics stream, and a mixed xylene stream in the splitter unit, introducing the toluene stream, the C9 aromatics stream, and a hydrogen stream into a transalkylation reactor, reacting the toluene stream and the C9 aromatics stream in the presence
(Continued)

of the transalkylation catalyst to produce a transalkylation effluent, introducing the transalkylation effluent to the splitter unit, and separating the transalkylation effluent in the splitter unit.

26 Claims, 9 Drawing Sheets

(51) Int. Cl.
| | |
|---|---|
| C10G 45/72 | (2006.01) |
| C07C 6/12 | (2006.01) |
| C10G 45/44 | (2006.01) |
| C10G 47/00 | (2006.01) |
| C10G 65/04 | (2006.01) |

(52) U.S. Cl.
CPC ............ *C10G 45/72* (2013.01); *C10G 47/00* (2013.01); *C10G 65/043* (2013.01); *B01J 2219/00027* (2013.01); *B01J 2219/00051* (2013.01); *C10G 2400/30* (2013.01)

(58) Field of Classification Search
CPC ..... C07C 5/2732; C07C 5/277; C07C 15/073; C07C 5/333; C07C 2/64; C07C 5/10
See application file for complete search history.

(56) References Cited

U.S. PATENT DOCUMENTS

| | | | |
|---|---|---|---|
| 4,172,813 A | 10/1979 | Bertolacini et al. | |
| 4,310,715 A | 1/1982 | Dorawala et al. | |
| 5,004,854 A | 4/1991 | Yan | |
| 5,030,787 A | 7/1991 | Absil et al. | |
| 5,763,720 A | 6/1998 | Buchanan et al. | |
| 5,847,256 A | 12/1998 | Ichioka et al. | |
| 5,866,741 A | 2/1999 | Wu et al. | |
| 5,942,651 A | 8/1999 | Beech, Jr. et al. | |
| 5,952,536 A | 9/1999 | Nacamuli et al. | |
| 6,024,422 A | 2/2000 | Drennen et al. | |
| 6,096,938 A | 8/2000 | Ghosh | |
| 6,204,422 B1 | 3/2001 | Tsutsui et al. | |
| 6,359,184 B1 | 3/2002 | Kato et al. | |
| 6,706,937 B2 | 3/2004 | Xiao et al. | |
| 7,288,687 B1 | 10/2007 | Frey et al. | |
| 7,544,849 B2 | 6/2009 | Boldingh et al. | |
| 7,563,358 B2 | 7/2009 | Stavens et al. | |
| 7,663,010 B2 | 2/2010 | Levin | |
| 7,727,490 B2 | 6/2010 | Zhou | |
| 8,071,828 B2 | 12/2011 | Cao et al. | |
| 8,084,657 B2 | 12/2011 | Kong et al. | |
| 8,183,424 B2 | 5/2012 | Levin et al. | |
| 8,198,502 B2 | 6/2012 | Bresler et al. | |
| 8,431,758 B2 | 4/2013 | Frey et al. | |
| 8,822,747 B2 | 9/2014 | Corradi et al. | |
| 9,000,247 B2 | 4/2015 | Abudawoud | |
| 9,249,068 B2 * | 2/2016 | Tinger ................ B01J 19/2445 | |
| 9,295,970 B1 | 3/2016 | Tinger et al. | |
| 9,302,953 B2 | 4/2016 | Molinier et al. | |
| 9,469,579 B2 | 10/2016 | Molinier et al. | |
| 2005/0197518 A1 | 9/2005 | Miller et al. | |
| 2007/0203376 A1 | 8/2007 | Negiz et al. | |
| 2008/0021253 A1 | 1/2008 | Corma Canos et al. | |
| 2009/0112034 A1 | 4/2009 | Levin | |
| 2012/0024755 A1 | 2/2012 | Beech, Jr. et al. | |
| 2012/0083638 A1 | 4/2012 | Boldingh et al. | |
| 2014/0100402 A1 | 4/2014 | Gawlik et al. | |
| 2015/0094508 A1 | 4/2015 | Corradi et al. | |
| 2016/0185686 A1 | 6/2016 | Molinier et al. | |

FOREIGN PATENT DOCUMENTS

| | | |
|---|---|---|
| WO | WO2012006039 A1 | 1/2012 |
| WO | 2013158956 A1 | 10/2013 |
| WO | WO2013158956 A1 | 10/2013 |

OTHER PUBLICATIONS

International Search Report and the Written Opinion for International Application No. PCT/US2013/037304 dated Jul. 4, 2013; pp. 1-9.
International Search Report and Written Opinion for International Application No. PCT/US2018/012129; International Filing Date Jan. 3, 2018; dated Apr. 24, 2018 (pp. 1-14).
Johnson, James A.; "Aromatics Complexes", Handbook of Petroleum Refining Processes Third Edition, 2004, Chapter 2.1, pp. 2.3-2.11.
Negiz, Antoine and Stoodt, Thomas J.; "UOP Tatoray Process", Handbook of Petroleum Refining Processes Third Edition, 2004, Chapter 2.7, pp. 2.55-2.63.
Silady, Ptrick J.; "UOP Isomar Process", Handbook of Petroleum Refining Processes Third Edition, 2004, Chapter 2.5, pp. 2.39-2.46.
PCT/US2018/032874 International Search Report and Written Opinion dated Jul. 5, 2018; 13 pgs.

* cited by examiner

PROCESS FOR MAXIMIZING XYLENES PRODUCTION FROM HEAVY AROMATICS FOR USE THEREIN

CROSS REFERENCE TO RELATED APPLICATIONS

This application is a continuation of and claims priority from U.S. Non-Provisional application Ser. No. 15/606,600 filed on May 26, 2017. For purposes of United States patent practice, this application incorporates the contents of the Non-Provisional application by reference in its entirety.

TECHNICAL FIELD

Disclosed are methods and systems for production of xylenes. Specifically, disclosed are methods and systems for production of xylenes from heavy aromatics.

BACKGROUND

Heavy reformate can include greater than 90 percent by weight (wt %) aromatics with eight or more carbon atoms in the aromatic compound. Of the aromatics, less than or equal to 10 wt % can be xylenes. In past practice, the heavy reformate was blended into the gasoline stream. However, blending is becoming more difficult due to more stringent regulations on the aromatics content in gasoline.

Para-xylene (p-xylene) is experiencing a market growth rate of demand. Consequently, the conversion of heavy aromatics to p-xylene provides a valuable product stream.

SUMMARY

Disclosed are methods and systems for production of xylenes. Specifically, disclosed are methods and systems for production of xylenes from heavy aromatics.

In a first aspect, a method for producing xylenes from a heavy reformate feed is provided. The method includes the steps of introducing the heavy reformate feed and a hydrogen feed to a dealkylation reactor. The dealkylation reactor includes a dealkylation catalyst. The heavy reformate includes aromatic hydrocarbons with nine or more carbon atoms (C9+ aromatics) and the hydrogen feed includes hydrogen gas. The method further includes the steps of reacting the heavy reformate feed with the hydrogen gas in the presence of the dealkylation catalyst in the dealkylation reactor to produce a dealkylation effluent, where the dealkylation reactor is at a dealkylation temperature, a dealkylation pressure, and the dealkylation reactor has a liquid hourly space velocity, introducing the dealkylation effluent to a splitter unit, where the dealkylation effluent includes light gases, toluene, benzene, mixed xylenes, and C9+ aromatics, separating the dealkylation effluent into a light gas stream, a toluene stream, a benzene stream, a C9 aromatics stream, a C10+ aromatics stream, and a mixed xylene stream in the splitter unit. The light gas stream includes light hydrocarbons and hydrogen, the toluene stream includes toluene, the benzene stream includes benzene, the mixed xylene stream includes mixed xylenes, and the C9 aromatics stream includes C9 aromatics, and the C10+ aromatics stream includes C10+ aromatics. The method further includes the steps of introducing the toluene stream, the C9 aromatics stream, and a hydrogen stream into a transalkylation reactor, where the transalkylation reactor includes a transalkylation catalyst, where the hydrogen stream includes hydrogen gas, reacting the toluene stream and the C9 aromatics stream in the presence of the transalkylation catalyst to produce a transalkylation effluent, where the transalkylation reactor is at a transalkylation temperature, a transalkylation pressure, and the transalkylation reactor has a liquid hourly space velocity, introducing the transalkylation effluent to the splitter unit, where the transalkylation effluent includes light gases, toluene, benzene, mixed xylenes, and C9+ aromatics, and separating the transalkylation effluent in the splitter unit such that mixed xylenes in the transalkylation effluent exit the splitter unit as part of the mixed xylene stream.

In certain aspects, the method further includes the steps of introducing the light gas stream to a gas separator and separating the light gas stream into a produced hydrogen and a light gas product. In certain aspects, the method further includes the step of introducing the benzene stream to the transalkylation reactor. In certain aspects, the method further includes the step of supplying an added aromatic stream to the transalkylation reactor, such that there is an excess of toluene for transalkylation reactions in the transalkylation reactor. In certain aspects, the dealkylation temperature is between 200 degrees Celsius (deg C.) and 500 deg C. In certain aspects, the dealkylation pressure is between 5 bar and 40 bar. In certain aspects, the liquid hourly space velocity in the dealkylation reactor is between 1 per hour ($hr^{-1}$) and 10 $hr^{-1}$. In certain aspects, the transalkylation temperature is between 300 deg C. and 500 deg C. In certain aspects, the transalkylation pressure is between 10 bar and 40 bar. In certain aspects, the liquid hourly space velocity in the transalkylation reactor is between 0.5 $hr^{-1}$ and 6 $hr^{-1}$.

In a second aspect, an apparatus for producing xylenes from a heavy reformate feed is provided. The apparatus includes a dealkylation reactor configured to convert a heavy reformate feed and a hydrogen feed in the presence of a dealkylation catalyst to produce a dealkylation effluent, a splitter unit fluidly connected to the dealkylation reactor and configured to separate the dealkylation effluent and a transalkylation effluent into a light gas stream, a toluene stream, a benzene stream, a C9 aromatics stream, a C10+ aromatics stream, and a mixed xylene stream, and the transalkylation reactor fluidly connected to the splitter unit and configured to convert the C9 aromatics stream, the toluene stream, and a hydrogen stream in the presence of a transalkylation catalyst to a transalkylation effluent.

In certain aspects, the apparatus further includes a gas separator fluidly connected to the splitter unit and configured to separate the light gas stream into a produced hydrogen and a light gas product.

BRIEF DESCRIPTION OF THE DRAWINGS

These and other features, aspects, and advantages of the scope will become better understood with regard to the following descriptions, claims, and accompanying drawings. It is to be noted, however, that the drawings illustrate only several embodiments and are therefore not to be considered limiting of the scope as it can admit to other equally effective embodiments.

Figure 1:
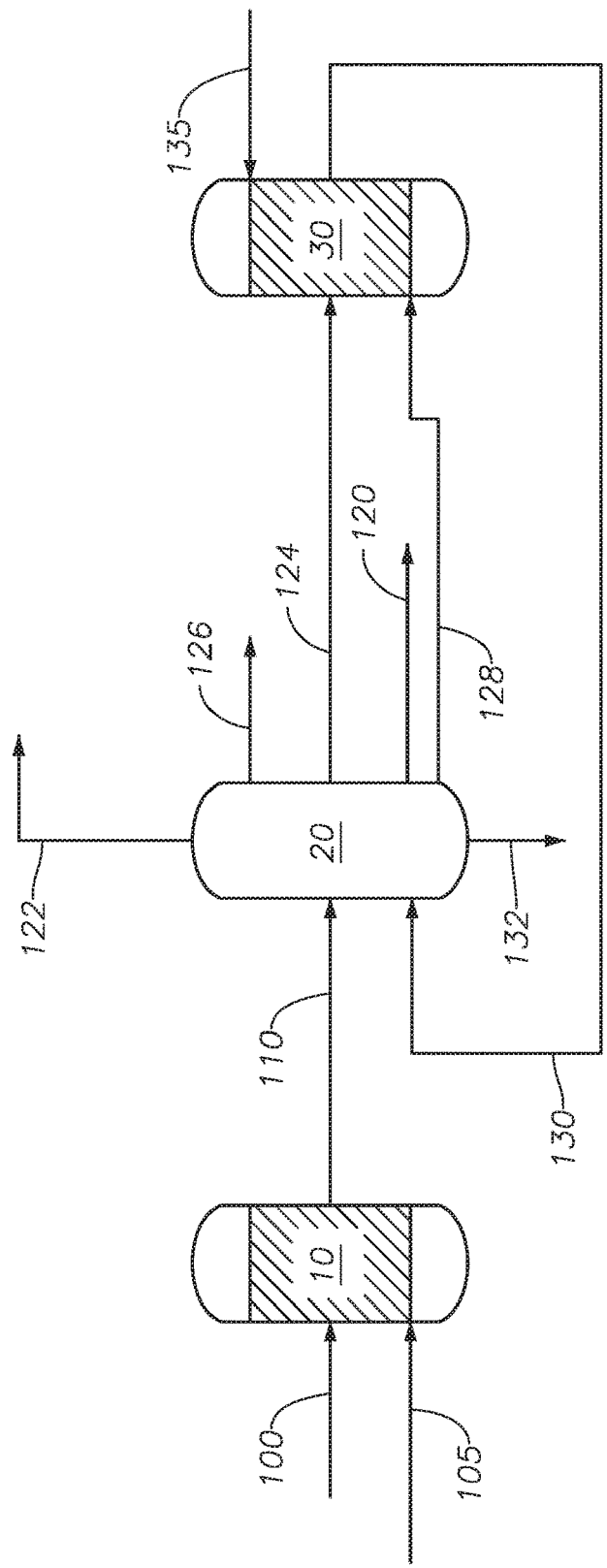
FIG. 1 provides a process diagram of an embodiment of the process.

In the accompanying Figures, similar components or features, or both, may have a similar reference label.

DETAILED DESCRIPTION

While the scope of the apparatus and method will be described with several embodiments, it is understood that one of ordinary skill in the relevant art will appreciate that many examples, variations and alterations to the apparatus and methods described here are within the scope and spirit of the embodiments.

Accordingly, the embodiments described are set forth without any loss of generality, and without imposing limitations, on the embodiments. Those of skill in the art understand that the scope includes all possible combinations and uses of particular features described in the specification.

Described here are processes and systems of a three unit system for the production of mixed xylenes. A heavy reformate is introduced to a dealkylation reactor. The dealkylation effluent from the dealkylation reactor is introduced to a splitter unit to separate the components of the dealkylation effluent. The toluene and C9+ aromatics from the splitter unit are introduced to a transalkylation reactor. Optionally, the benzene can be introduced to the transalkylation reactor also. The transalkylation effluent from the transalkylation reactor is introduced to the splitter unit to separate the components of the transalkylation effluent. The streams exiting the splitter unit include the components of the effluents from both the dealkylation reactor and the transalkylation reactor.

Advantageously, the combination of a dealkylation reactor and a separate transalkylation reactor increases the overall production of xylenes as compared to a one-reactor system that contains both a dealkylation catalyst and a transalkylation catalyst or a single catalyst capable of both dealkylation and transalkylation reactions. Advantageously, recycling the transalkylation effluent to the splitter unit increases overall yield because it minimizes the loss of xylene by reducing the production of benzene through disproportionation of toluene in the transalkylation reactor. There are two primary reactions that occur in the transalkylation reactor to form xylene, an equilibrium transalkylation reaction of toluene and trimethylbenzene and an equilibrium disproportionation reaction of toluene:

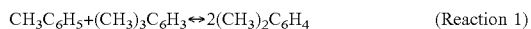

(Reaction 1)

(Reaction 2)

Recycling benzene will limit the production of benzene through Reaction 2, reducing the consumption of toluene in Reaction 2 making more toluene available for the production of xylene in Reaction 1.

As used throughout, a reference to "C" and a number refers to the number of carbon atoms in a hydrocarbon. For example, C1 refers to a hydrocarbon with one carbon atom and C6 refers to a hydrocarbon with six carbon atoms.

As used throughout, "C9 aromatics" refers to aromatic hydrocarbons with nine carbon atoms. Examples of C9 aromatic hydrocarbons include methylethylbenzene, trimethylbenzene, and propylbenzene.

As used throughout, "trimethylbenzene" includes each of the isomers of trimethylbenzene: hemellitene, pseudocumene, and mesitylene.

As used throughout, "C10+ aromatics" refers to aromatic hydrocarbons with ten carbon atoms and aromatics with more than ten carbon atoms, such as an aromatic hydrocarbon with eleven carbon atoms.

As used throughout, "C9+ aromatics" refers to the group of C9 aromatics and C10+ aromatics.

As used throughout, "mixed xylenes" refers to one or more of para-xylene (p-xylene), meta-xylene (m-xylene), and ortho-xylene (o-xylene).

As used throughout, "dealkylation reaction" refers to a reaction that results in the removal of an alkyl group from one or more of the reactants.

As used throughout, "transalkylation reaction" refers to a reaction that results in the transfer of an alkyl group from one or compound to another.

As used throughout, "light hydrocarbons" refers to one or more of alkanes, including methane, ethane, propane, butanes, pentanes, alkenes, and trace amounts of naphthenes, such as cyclopentane, cyclohexane.

As used throughout, "light gases" refers to one or more of light hydrocarbons, hydrogen, and air.

Referring to FIG. 1 an embodiment of the process for producing mixed xylenes in provided. Heavy reformate feed 100 is introduced to dealkylation reactor 10 along with hydrogen feed 105. Heavy reformate feed 100 can include toluene, mixed xylenes, C9 aromatics, and C9+ aromatics. In at least one embodiment, heavy reformate feed 100 can include trace amounts of C8+ naphthenes and C10+ naphthylenes, including the alkyl derivatives of the same. In at least one embodiment, heavy reformate feed 100 can contain between 0 wt % and 10 wt % mixed xylenes and between 60 wt % and 100 wt % C9+ aromatics. In at least one embodiment, heavy reformate feed 100 can contain between 0 wt % and 60 wt % toluene. In at least one embodiment, heavy reformate feed 100 can contain between 0 wt % and 10 wt % mixed xylenes, between 0 wt % and 60 wt % toluene, and between 60 wt % and 100 wt % C9+ aromatics. In at least one embodiment, heavy reformate feed 100 contains between 60 wt % and 100 wt % C9 aromatics and is in the absence of C10+ aromatics.

Hydrogen feed 105 can be any stream containing hydrogen gas. Hydrogen feed 105 can be a stream of pure hydrogen from a fresh hydrogen source. In at least one embodiment described with reference to FIG. 2, hydrogen gas can be recovered from the process in gas separator 40 as produced hydrogen 145, which can be divided such that a portion of produced hydrogen 145 can be recycled as hydrogen feed 105 and introduced to dealkylation reactor 10. In at least one embodiment, hydrogen feed 105 can be from a hydrogen source in a refinery and can contain light hydrocarbons.

Returning to FIG. 1, dealkylation reactor 10 can be any type of reactor capable of containing and supporting a dealkylation reaction. Dealkylation reactor 10 can be a fixed bed reactor or a fluidized bed reactor. The dealkylation temperature in dealkylation reactor 10 can be between 200 degrees Celsius (deg C.) and 500 deg C. The dealkylation pressure in dealkylation reactor 10 can be between 5 bar (500 kilopascal (kPa)) and 40 bar (4000 kPa). The liquid hourly space velocity (LHSV) can be between 1 per hour $(hr^{-1})$ and 10 $hr^{-1}$.

Dealkylation reactor 10 can include a dealkylation catalyst. The dealkylation catalyst can include any catalysts capable of catalyzing dealkylation reactions. Examples of dealkylation catalyst can include bifunctional catalysts such as those described in U.S. Pat. No. 9,000,247. The dealkylation catalyst can be selected to selectively convert one or more of the C9+ aromatics over the others in dealkylation reactions. Dealkylation reactions can convert C9+ aromatics to toluene, benzene, mixed xylenes, and light gases; and can convert C10+ aromatics to C9+ aromatics. Reactions in dealkylation reactor 10 can remove methyl, ethyl, propyl, butyl and pentyl groups, and their isomers, attached to C10+ aromatics. In at least one embodiment, a dealkylation catalyst can be selected to convert more than 97.5 wt % of the methylethylbenzene to toluene. In at least one embodiment, the overall conversion of C9+ aromatics can be above 98 wt % due to conversion of C9 aromatics and the removal of methyl, ethyl, propyl, butyl and pentyl groups attached to C10+ aromatics. Dealkylation effluent 110 can contain mixed xylenes, toluene, benzene, light gases, and C9+ aromatics.

In at least one embodiment, where hydrogen feed 105 is introduced to dealkylation reactor 10, dealkylation reactor 10 is a fixed bed reactor and the light gases produced in dealkylation effluent 110 contain alkanes. In at least one embodiment, dealkylation reactor 10 is in the absence of a hydrogen stream (not shown), dealkylation reactor 10 is a fluidized bed reactor and the light gases produced in dealkylation effluent 110 contain alkenes.

Dealkylation effluent 110 is introduced to splitter unit 20.

Splitter unit 20 can be any type of separation unit capable of separating a stream into its component parts. In at least one embodiment, splitter unit 20 can be one splitter column designed to separate the feed stream into multiple split streams. In at least one embodiment, splitter unit 20 can be multiple splitter columns in series designed to separate one component from the feed stream. In at least one embodiment, splitter unit 20 can be one or more distillation units. In at least one embodiment, where splitter unit 20 is multiple splitter columns, splitter unit 20 includes five splitter columns: a first column operates at a pressure of between 4 bar gauge (barg) and 6 barg and a temperature between 100 deg C. and 200 deg C. to separate light gases from the first column feed to produce light gas stream 122 and a first column effluent; a second column operates at a pressure of between 0.6 barg and 1.5 barg and a temperature between 100 deg C. and 170 deg C. to separate benzene and toluene from the first column effluent to produce a benzene/toluene stream and a second column effluent; a third column operates at a pressure of between 0.3 barg and 0.9 barg and a temperature between 70 deg C. and 150 deg C. to separate benzene from the benzene/toluene stream to produce benzene stream 126 and to separate toluene from the benzene toluene stream to produce toluene stream 124; a fourth column operates at a pressure of between 0.3 barg and 2 barg and a temperature between 120 deg C. and 210 deg C. to separate xylenes from the second column effluent to produce mixed xylene stream 120 and a C9+ aromatics stream; and a fifth column operates at a pressure of between 0.5 barg and 3 barg and a temperature of between 150 deg C. and 250 deg C. to separate C9 aromatics from the C9+ aromatics stream to produce C9 aromatics stream 128 and to separate C10+ aromatics from the C9+ aromatics stream to produce C10+ aromatics stream 132. In at least one embodiment, where splitter unit 20 is multiple splitter columns, splitter unit 20 can be in the absence of a column to separate C9 aromatics from C10+ aromatics, such that the column to separate xylenes produces the xylene stream and a C9+ stream. The C9+ stream can be introduced to the transalkylation reactor. In at least one embodiment, where splitter unit 20 is multiple splitter columns, splitter unit 20 can be in the absence of a column to separate benzene/toluene stream. It can be understood by one of skill in the art that splitter unit 20 can be designed to operate at a temperature and pressure to produce the desired streams. In at least one embodiment, where splitter unit 20 is one distillation column, the distillation column can include multiple sections in one vessel, where each section has the operating conditions corresponding to each of the separate columns described in this paragraph.

Splitter unit 20 separates the components to produce mixed xylene stream 120, light gas stream 122, toluene stream 124, benzene stream 126, C9 aromatics stream 128, and C10+ aromatics stream 132. Mixed xylene stream 120 contains mixed xylenes. Light gas stream 122 contains light gases. Toluene stream 124 contains toluene. Benzene stream 126 contains benzene. C9 aromatics stream 128 contains C9 aromatics, including C9 aromatics formed in dealkylation reactor 10 and unreacted C9 aromatics from heavy reformate feed 100. C10+ aromatics stream 132 contains C10+ aromatics, including C10+ aromatics formed in dealkylation reactor 10 and unreacted C10+ aromatics from heavy reformate feed 100. In at least one embodiment, C10+ aromatics stream 132 can be purged from the system. In at least one embodiment, C10+ aromatics stream 132 can be introduced to dealkylation reactor 10 for further processing to increase the conversion of C10+ aromatics.

Advantageously, the separation and removal of mixed xylenes in the splitter unit increases production of mixed xylenes in the transalkylation reactor. The absence of mixed xylenes in the feed to transalkylation reactor 30 drives the thermodynamic equilibrium of Reaction 1 towards xylene production in transalkylation reactor 30.

Toluene stream 124 and C9 aromatics stream 128 are introduced to transalkylation reactor 30 along with hydrogen stream 135. Hydrogen stream 135 can be any stream containing hydrogen gas. Hydrogen stream 135 can be a stream of pure hydrogen from a fresh hydrogen source. In at least one embodiment described with reference to FIG. 2, produced hydrogen 145 can be divided such that a portion of produced hydrogen 145 can be recycled as hydrogen feed 105 and introduced to dealkylation reactor 10 and a second portion of produced hydrogen can be recycled as hydrogen stream 135 and introduced to transalkylation reactor 30.

Transalkylation reactor 30 can be a fixed bed reactor or a fluidized bed reactor. The transalkylation temperature in transalkylation reactor 30 can be between 300 deg C. and 500 deg C. The transalkylation pressure in transalkylation reactor 30 can be between 10 bar (1000 kPa) and 40 bar (4000 kPa). The liquid hourly space velocity (LHSV) can be between 0.5 $hr^{-1}$ and 6 $hr^{-1}$. The operating conditions can be set to maximize the production of xylenes. The temperature can have a greater influence on the transalkylation reaction than pressure. It is understood that higher temperatures, higher pressures, and lower LHSV favor transalkylation reactions, while higher temperatures can lead to catalyst deactivation and therefore, the operating conditions must be balanced to maximize production and minimize catalyst deactivation.

Transalkylation reactor 30 can include a transalkylation catalyst. The transalkylation catalyst can include any catalyst capable of catalyzing transalkylation reactions. Examples of transalkylation catalysts include bifunctional catalysts as described in U.S. Pat. No. 9,000,247. The transalkylation catalyst can be selected to selectively convert one or more of the C9+ aromatics over the others in transalkylation reactions. In at least one embodiment, the transalkylation catalyst can be selected to selectively convert trimethylbenzenes to mixed xylenes. Transalkylation reactions can occur to convert C9+ aromatics to toluene, benzene, mixed xylenes, and light gases. Transalkylation effluent 130 contains mixed xylenes, toluene, benzene, light gases, and C9+ aromatics.

Figure 3:
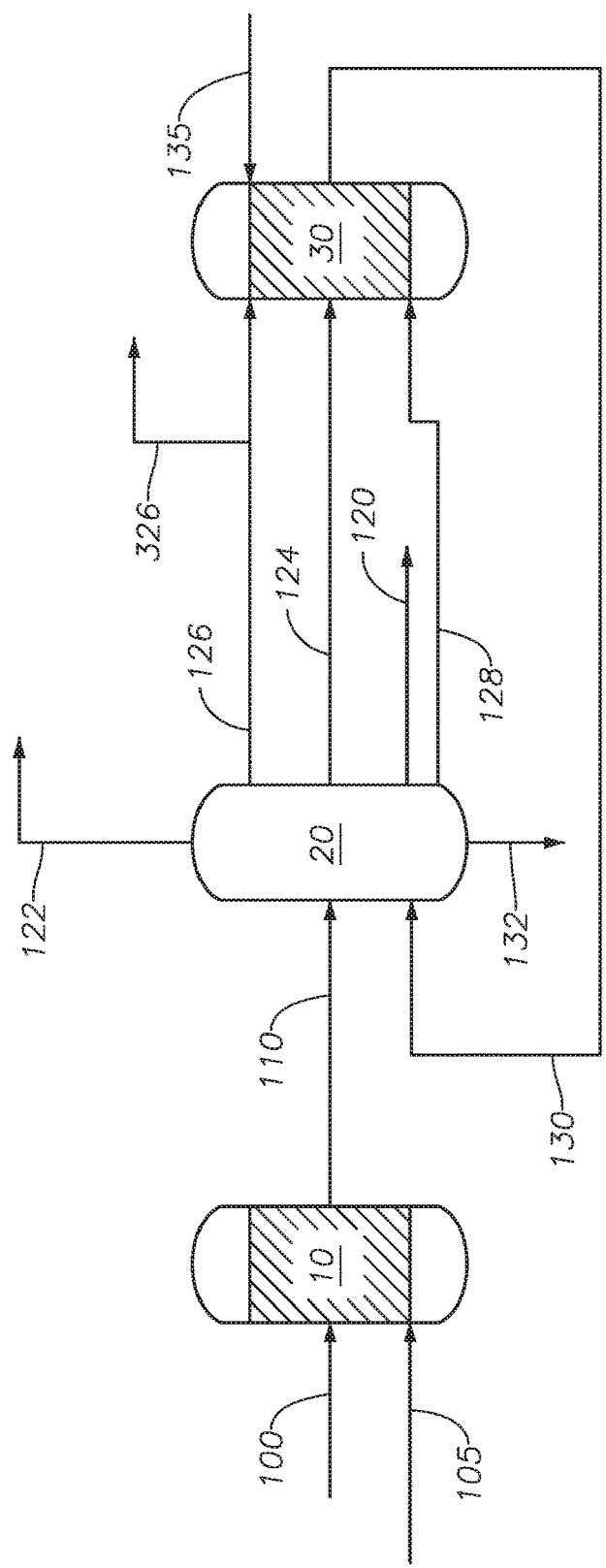
FIG. 3 provides a process diagram of an embodiment of the process.

In at least one embodiment, with reference to FIG. 3, benzene stream 126 can be introduced to transalkylation reactor 30. In at least one embodiment, a slip stream can be removed from benzene stream 126 as benzene product 326. The volume of benzene stream 126 introduced to transalkylation reactor 30 can be determined based on the reaction conditions desired in transalkylation reactor 30. In at least one embodiment, the volume of benzene stream 126 introduced to transalkylation reactor 30 can be controlled by the flow rate of benzene product 326. Adding benzene from benzene stream 126 to transalkylation reactor 30 can minimize the production of benzene through Reaction 2 and increase the production of mixed xylenes through Reaction 1.

Transalkylation reactor 30 produces transalkylation effluent 130. Transalkylation effluent 130 can contain mixed xylenes, toluene, benzene, light gases, and C9+ aromatics, including C9+ aromatics formed in transalkylation reactor 30 and unreacted C9+ aromatics from heavy reformate feed 100.

Transalkylation effluent 130 can be introduced to splitter unit 20. Transalkylation effluent 130 is separated in splitter unit 20 and the component parts form part of mixed xylene stream 120, light gas stream 122, toluene stream 124, benzene stream 126, C9 aromatics stream 128, and C10+ aromatics stream 132.

The overall yield of mixed xylenes in mixed xylene stream 120 can be between 30 wt % and 89 wt %. In at least one embodiment, the overall yield of mixed xylenes in mixed xylene stream 120 is 80 wt %. The overall yield of toluene can be between 0 wt % and 20 wt % and alternately between 5 wt % and 20 wt %. The overall yield of benzene can be between 0 wt % and 10 wt % and alternately between 1 wt % and 10 wt %. Mixed xylene stream 120 can be introduced to an isomerization unit or a crystallization unit to convert m-xylene and o-xylene to p-xylene.

Figure 2:
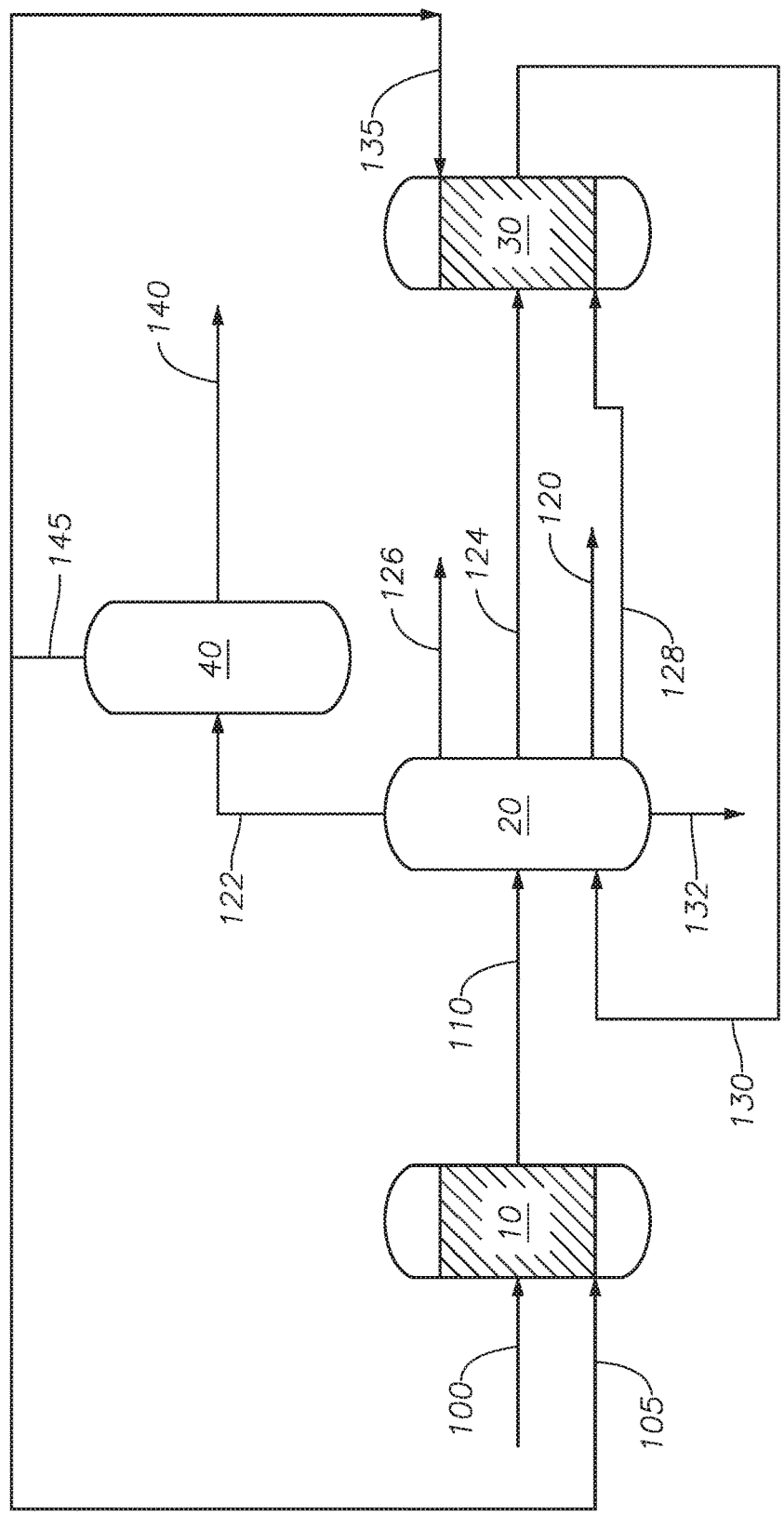
FIG. 2 provides a process diagram of an embodiment of the process.

Referring to FIG. 2, an embodiment of the process to produce mixed xylenes is provided. Light gas stream 122 is introduced to gas separator 40. Gas separator 40 can be any type of separation unit capable of separating hydrogen from a stream of gases. In at least one embodiment, gas separator 40 is a pressure swing adsorption unit. In at least one embodiment, gas separator 40 is a hydrogen membrane separation unit. Gas separator 40 can separate light gas stream 122 into light gas product 140 and produced hydrogen 145. Produced hydrogen 145 can be split to create hydrogen feed 105 and hydrogen stream 135. Light gas product 140 contains light hydrocarbons. Produced hydrogen 145 contains hydrogen. Light gas product 140 can be purged to the atmosphere, used as a source fuel, or sent for further processing.

Figure 4:
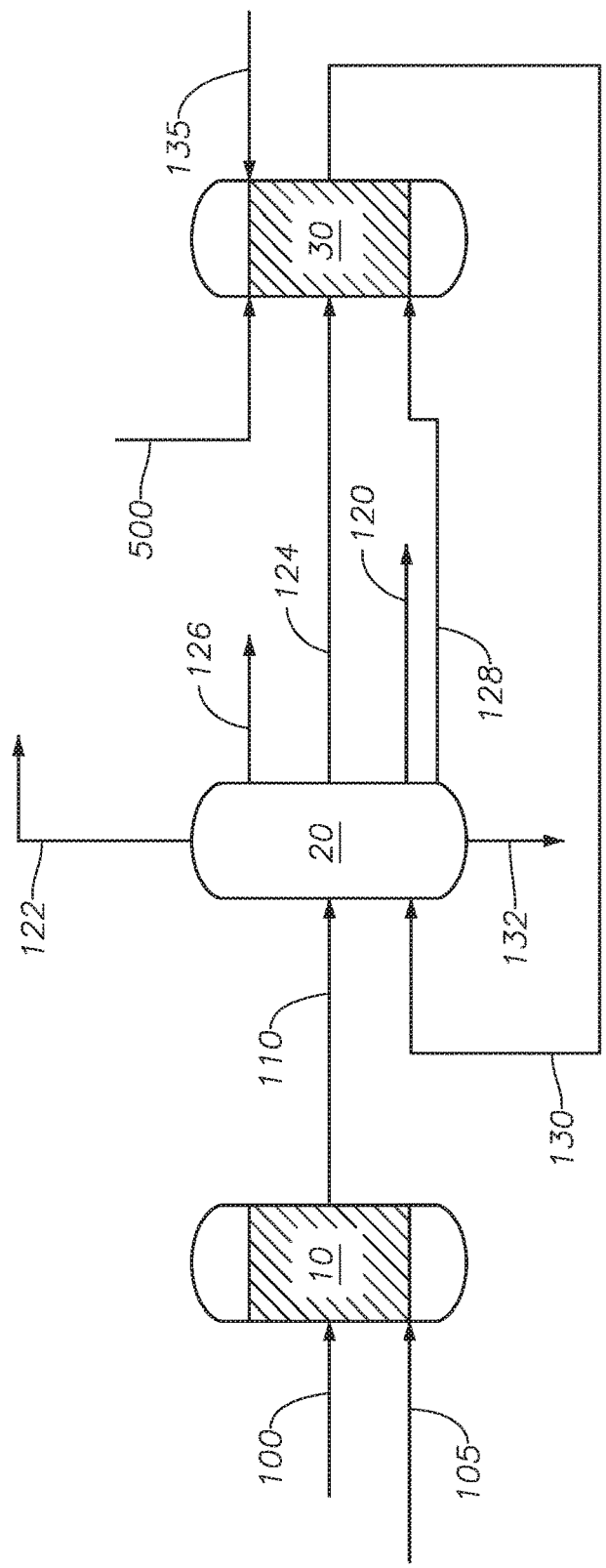
FIG. 4 provides a process diagram of an embodiment of the process.

Referring to FIG. 4, an embodiment of the process to produce mixed xylenes is provided with reference to FIG. 1. Added aromatic stream 500 is introduced to transalkylation reactor 30. Added aromatic stream 500 can include toluene, benzene, or combinations of the same. In at least one embodiment, added aromatic stream 500 includes toluene. The flow rate of added aromatic stream 500 can be at a volume to provide surplus toluene to increase conversion of trimethylbenzene in the reaction between toluene and trimethylbenzene present in C9 aromatics stream 128. Added aromatic stream 500 can be used to increase the methyl group to aromatic ratio to 2, which can increase the conversion of C9 aromatics to xylenes. In at least one embodiment, dealkylation reactor 10 is in the absence of an added aromatic stream.

In at least one embodiment, the dealkylation reactor and the transalkylation reactor can be housed in one vessel, where the two reactor stages are physically separate from each other with no mingling of the internal gases. The effluent from the dealkylation reactor stage can exit the vessel and enter a splitter unit where the benzene stream, toluene stream, and C9 aromatics stream can be separated and then reintroduced to the vessel in the transalkylation reactor stage.

Advantageously, the position of the dealkylation reactor upstream of the transalkylation produces toluene not present in the heavy reformate feed, toluene is a reactant in transalkylation reactions to produce xylene, thus a process with the dealkylation reactor upstream of the transalkylation increases xylene production. Advantageously, the position of the dealkylation reactor upstream of the transalkylation reactor reduces the amount of C9 aromatics and C10+ aromatics being introduced to the transalkylation reactor.

Both the dealkylation reactor and the transalkylation reactor are in the absence of methanol and in the absence of methylation reactions, which are irreversible reactions that add a methyl group to a compound. In at least one embodiment, the heavy reformate feed is in the absence of ethylbenzene.

EXAMPLES

The following examples were carried out in laboratory equipment.

Example 1

Example 1 provides an analysis of dealkylation reactor 10 with reference to FIG. 2. Heavy reformate feed 100 had the composition in Table 1. Hydrogen feed 105 was recycled from produced hydrogen 145 after being recovered from gas separator 40.

TABLE 1

| Composition of heavy reformate feed 100 | |
|---|---|
| Component | Composition, wt % |
| Ethylbenzene | 0.0498 |
| Mixed xylenes | 5.1789 |
| C9 aromatics total | 80.1502 |
| Trimethylbenzene | 56.5475 |
| Methylethylbenzene | 21.0869 |
| Propylbenzene | 2.5158 |
| C10+ aromatics | 14.6211 |

Dealkylation reactor 10 was at a temperature of 400 deg C. and a pressure of 30 bar (3000 kPa). The weight hourly space velocity (whsv) was 4.2 per hour ($hr^{-1}$). The ratio of hydrogen gas ($H_2$) to hydrocarbons was 4:1 (mol/mol). The catalyst was a ZSM-5 catalyst designed for dealkylation reactions to selectively convert methylethylbenzenes to toluene, benzene, and light alkanes. The composition of dealkylation effluent 110 is shown in Table 2.

TABLE 2

Composition of dealkylation effluent 110

| Component | Composition, wt % |
|---|---|
| Light hydrocarbons | 7.00 |
| Benzene | 2.49 |
| Toluene | 16.26 |
| Ethylbenzene | 0.04 |
| Mixed xylenes | 16.49 |
| C9 aromatics total | 50.65 |
| Trimethylbenzene | 50.39 |
| Methylethylbenzene | 0.26 |
| Propylbenzene | 0 |
| C10+ aromatics | 7.08 |

The conversion of methylethylbenzene in dealkylation reactor 10 was 98.8 wt %. The conversion of trimethylbenzene in dealkylation reactor 10 was 10.9 wt %.

Example 2

Example 2 provides an analysis of transalkylation reactor 30 with reference to FIG. 2. The combined feed to transalkylation reactor 30 had the composition in Table 3.

TABLE 3

Composition of feed to transalkylation reactor 30

| Component | Composition, wt % |
|---|---|
| Toluene | 50 |
| Trimethylbenzene | 50 |

Transalkylation reactor 30 was at a temperature of 400 deg C. and a pressure of 30 bar (3000 kPa). The whsv was 4.2 hr$^{-1}$. The ratio of hydrogen gas (H$_2$) to hydrocarbons is 4:1 (mol/mol). The catalyst was a transalkylation catalyst with a zeolite. The composition of transalkylation effluent 130 is shown in Table 4.

TABLE 4

Composition of transalkylation effluent 130

| Component | Composition, wt % |
|---|---|
| Light hydrocarbons | 8.4 |
| Benzene | 3.9 |
| Toluene | 22.1 |
| Ethylbenzene | 0.3 |
| Mixed xylenes | 37 |
| C9 aromatics total | 20.8 |
| Trimethylbenzene | 19.9 |
| Methylethylbenzene | 0.9 |

TABLE 4-continued

Composition of transalkylation effluent 130

| Component | Composition, wt % |
|---|---|
| Propylbenzene | 0 |
| C10+ aromatics | 6.3 |

The conversion of trimethylbenzene in transalkylation reactor 30 was 56 wt %. The conversion of toluene in transalkylation reactor 30 was 52 wt %.

Example 3

Figure 5:
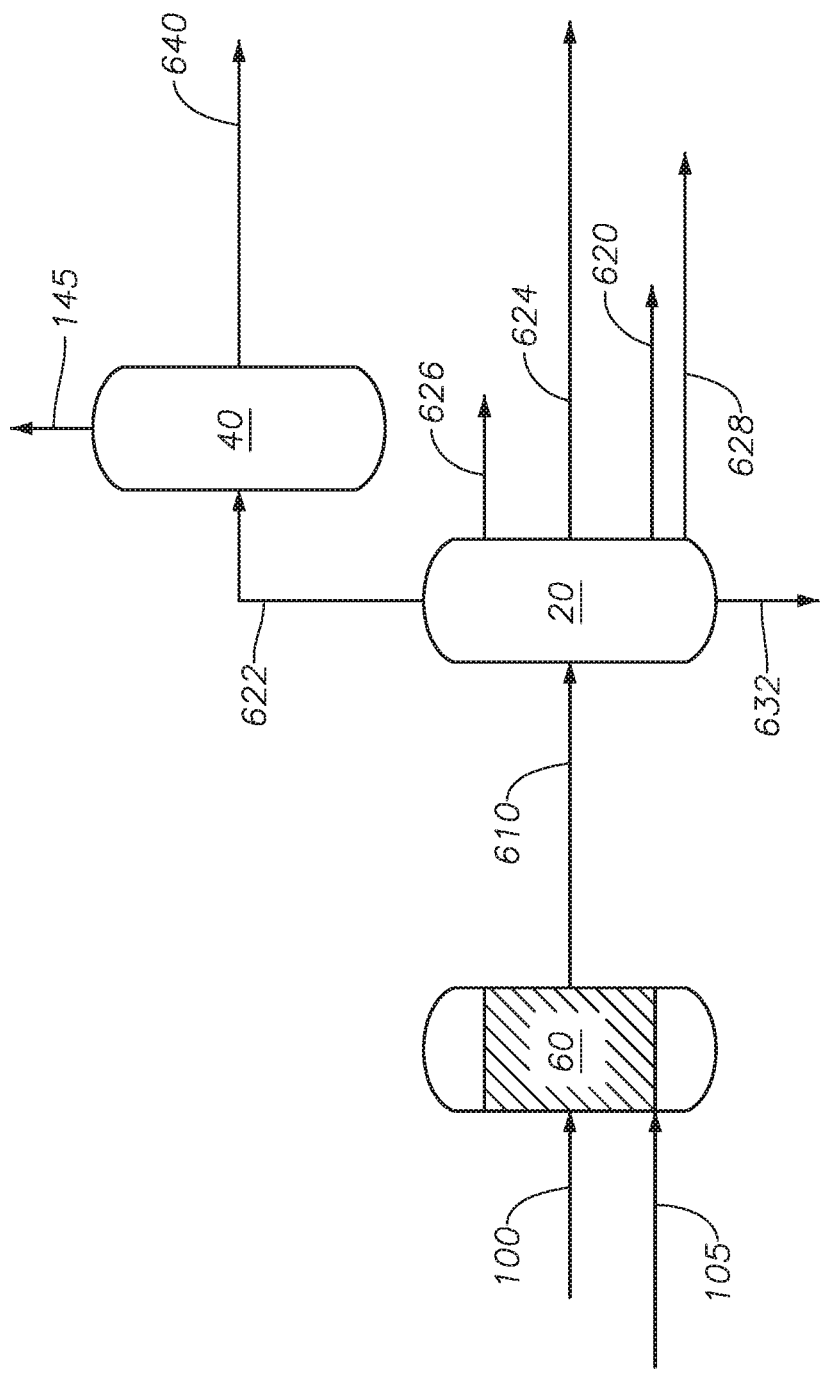
FIG. 5 provides a process diagram of a one-reactor system.

Example 3 was a comparative example of a one-reactor system, where dealkylation reactions and transalkylation reactions occur in the same reactor, coupled with a splitter unit described with reference to FIG. 5 and FIG. 2. Heavy reformate feed 100, having the composition described in Table 5, was introduced to transalkylation-dealkylation reactor 60 along with hydrogen feed 105. Hydrogen feed 105 was simulated as a feed from a hydrogen source in a refinery containing only hydrogen.

TABLE 5

Composition of heavy reformate feed 100

Composition, kilogram per hour (kg/hr)

| Component | Heavy Reformate Feed 100 | Hydrogen Feed 105 | Produced Hydrogen 145 |
|---|---|---|---|
| Hydrogen | 0 | 20 | 16.5 |
| Light hydrocarbons | 0 | 0 | 0 |
| Benzene | 0 | 0 | 0 |
| Toluene | 0 | 0 | 0 |
| Ethylbenzene | 0 | 0 | 0 |
| Mixed xylenes | 51 | 0 | 0 |
| C9 aromatics total | 835 | 0 | 0 |
| Trimethylbenzene | 592 | — | — |
| Methylethylbenzene | 213 | — | — |
| Propylbenzene | 30 | — | — |
| C10+ aromatics | 114 | 0 | 0 |

Transalkylation-dealkylation reactor 60 was operated at a temperature of 400 deg C., a pressure of 20 bar, a whsv of 4.2 hr$^{-1}$, and a hydrogen to hydrocarbon ratio of 4:1. The catalyst was a catalyst was a 40% beta and 60% MCM-41 catalyst that can facilitate both transalkylation and dealkylation reactions.

One-reactor effluent 610 was introduced to splitter unit 20. Splitter unit 20 operated to separate one-reactor effluent 610 into its component parts, as shown in Table 6. Light product 622 was introduced to gas separator 40 which separated hydrogen from light hydrocarbons to produce produced hydrogen 145 and gas product 640 containing light hydrocarbons.

TABLE 6

Composition of Streams Exiting Splitter Unit 20 in Example 3

Composition, kg/hr

| Component | Light gas 622 | Benzene 626 | Toluene 624 | Xylene 620 | C9 Aromatics 628 | C10+ Aromatics 632 |
|---|---|---|---|---|---|---|
| Hydrogen | 16.5 | 0 | 0 | 0 | 0 | 0 |
| Light hydrocarbons | 20.6 | 0 | 0 | 0 | 0 | 0 |
| Benzene | 0 | 12.0 | 0 | 0 | 0 | 0 |
| Toluene | 0 | 0 | 113.6 | 0 | 0 | 0 |
| Ethylbenzene | 0 | 0 | 0 | 3.6 | 0 | 0 |

TABLE 6-continued

Composition of Streams Exiting Splitter Unit 20 in Example 3

| | Composition, kg/hr | | | | | |
|---|---|---|---|---|---|---|
| Component | Light gas 622 | Benzene 626 | Toluene 624 | Xylene 620 | C9 Aromatics 628 | C10+ Aromatics 632 |
| Mixed xylenes | 0 | 0 | 0 | 339.7 | 0 | 0 |
| C9 aromatics total | 0 | 0 | 0 | 0 | 366.7 | 0 |
| Trimethylbenzene | — | — | — | — | 324.9 | — |
| Methylethylbenzene | — | — | — | — | 41.7 | — |
| Propylbenzene | — | — | — | — | 0 | — |
| C10+ aromatics | 0 | 0 | 0 | 0 | 0 | 147.3 |

The mixed xylene yield was 34 wt %, which was in the range of xylene yield for a one-reactor system, of between 32 wt % and 35 wt %. In a one-reactor system, the production of xylene is limited by the thermodynamic equilibrium, as shown in Reaction 1. The conversion of methylethylbenzene was 80%, which falls within then typical range of methylethylbenzene conversion in a one-reactor system of between 80 wt % and 92 wt %. The conversion of trimethylbenzene was 45%, which was slightly outside of the typical range of trimethylbenzene conversion of around 50 wt %.

Example 4

Figure 6:
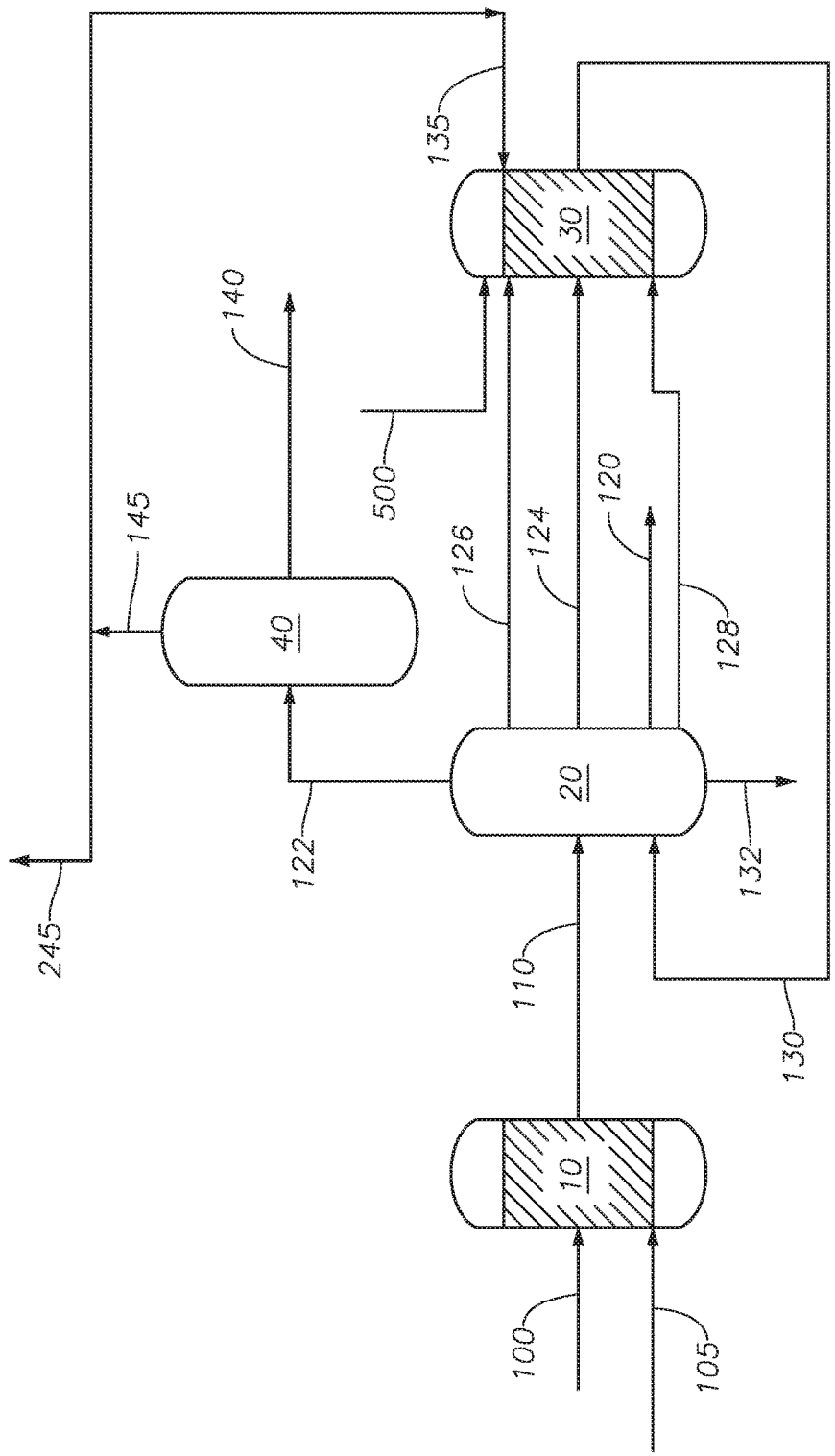
FIG. 6 provides a process diagram of an embodiment of the process.

Example 4 was a simulation of the process to produce mixed xylenes with reference to FIG. 6 and FIG. 2. Heavy reformate feed 100, having the composition in Table 7, is introduced to dealkylation reactor 10 along with hydrogen feed 105. The flow rate of hydrogen feed 105 was 138.6 kg/hr, with 66.5 kg/hr of hydrogen gas and 72.0 kg/hr light hydrocarbons.

TABLE 7

Composition of heavy reformate feed 100

| Component | Composition, kg/hr | Composition, wt % |
|---|---|---|
| Mass Flow | 1000.0 | 100 |
| Hydrogen | 0 | 0.0 |
| Light gases | 0 | 0.0 |
| Benzene | 0 | 0.0 |
| Toluene | 0 | 0.0 |
| Ethylbenzene | 0.5 | 0.0 |
| Mixed xylenes | 51.8 | 5.2 |
| m-xylene | 31.8 | 3.2 |
| o-xylene | 10.0 | 1.0 |
| p-xylene | 10.0 | 1.0 |
| C9 aromatics total | 801.6 | 80.2 |
| Trimethylbenzene | 565.5 | 56.5 |
| Methylethylbenzene | 210.9 | 21.1 |

TABLE 7-continued

Composition of heavy reformate feed 100

| Component | Composition, kg/hr | Composition, wt % |
|---|---|---|
| Propylbenzene | 25.2 | 2.5 |
| C10+ aromatics | 146.2 | 14.6 |

Dealkylation reactor 10 was at a temperature of 400 deg C. and a pressure of 30 bar (3000 kPa). The whsv was 4.2 $h^{-1}$. The ratio of hydrogen gas ($H_2$) to hydrocarbons was 4:1 (mol/mol). The catalyst was a 3-dimensional zeolite-based dealkylation catalyst. The composition of dealkylation effluent 110 is shown in Table 8.

TABLE 8

Composition of dealkylation effluent 110

| Component | Composition, kg/hr | Composition, wt % without hydrogen gas |
|---|---|---|
| Mass Flow | 1138.6 | — |
| Hydrogen | 63.0 | — |
| Light gases | 106.5 | 9.9 |
| Benzene | 26.8 | 2.5 |
| Toluene | 174.9 | 16.3 |
| Ethylbenzene | 0.4 | 0.0 |
| Mixed xylenes | 177.5 | 16.5 |
| m-xylene | 102.2 | 9.5 |
| o-xylene | 39.9 | 3.7 |
| p-xylene | 35.4 | 3.3 |
| C9 aromatics total | 506.4 | 47.1 |
| Trimethylbenzene | 503.8 | 46.8 |
| Methylethylbenzene | 2.5 | 0.2 |
| Propylbenzene | 0.0 | 0.0 |
| C10+ aromatics | 83.1 | 7.7 |

Dealkylation effluent 110 was introduced to splitter unit 20 which separated dealkylation effluent 110 into its component parts. Light gas stream 122 was introduced to gas separator 40 to produce light gas product 140 and produced hydrogen 145. Produced hydrogen 145 was split to produce hydrogen slipstream 245 and hydrogen stream 135. The composition and flow rates are shown in Table 9.

TABLE 9

Composition of streams

| | Composition, kg/hr | | | | |
|---|---|---|---|---|---|
| Component | Stream 122 | Stream 140 | Stream 145 | Stream 135 | Stream 245 |
| Mass Flow | 407.6 | 222.1 | 185.5 | 126.9 | 58.6 |
| Hydrogen | 185.5 | 0.0 | 185.5 | 126.9 | 58.6 |
| Light gases | 222.1 | 222.1 | 0.0 | 0.0 | 0.0 |

TABLE 9-continued

Composition of streams

Composition, kg/hr

| Component | Stream 122 | Stream 140 | Stream 145 | Stream 135 | Stream 245 |
|---|---|---|---|---|---|
| Benzene | 0.0 | 0.0 | 0.0 | 0.0 | 0.0 |
| Toluene | 0.0 | 0.0 | 0.0 | 0.0 | 0.0 |
| Ethylbenzene | 0.0 | 0.0 | 0.0 | 0.0 | 0.0 |
| Mixed xylenes | 0.0 | 0.0 | 0.0 | 0.0 | 0.0 |
| m-xylene | — | — | — | — | — |
| o-xylene | — | — | — | — | — |
| p-xylene | — | — | — | — | — |
| C9 aromatics total | 0.0 | 0.0 | 0.0 | 0.0 | 0.0 |
| Trimethylbenzene | — | — | — | — | — |
| Methylethylbenzene | — | — | — | — | — |
| Propylbenzene | — | — | — | — | — |
| C10+ aromatics | 0.0 | 0.0 | 0.0 | 0.0 | 0.0 |

Benzene stream 126, toluene stream 124, and C9 aromatics stream 128 were introduced to transalkylation reactor 30 along with added aromatic stream 500 and hydrogen stream 135. The flow rate of added aromatic stream 500 was 70.0 kg/hr of pure toluene which creates a surplus of toluene in transalkylation reactor 30. Transalkylation reactor 30 was at a temperature of 400 deg C. and a pressure of 30 bar (3000 kPa). The whsv was 4.2 h$^{-1}$. The ratio of hydrogen gas (H$_2$) to hydrocarbons is 4:1 (mol/mol). The catalyst was a 1-dimensional zeolite-based transalkylation catalyst. The transalkylation catalyst was not the same as the dealkylation catalyst. The composition of various streams are shown in Table 10.

TABLE 10

Composition of Streams

Composition, kg/hr (wt % calculated with no hydrogen gas)

| Component | Stream 120 | Stream 124 | Stream 126 | Stream 128 | Stream 132 | Stream 130 |
|---|---|---|---|---|---|---|
| Mass Flow | 844.8 | 537.4 | 62.8 | 1003.2 | 83.1 | 1800.3 |
| Hydrogen | 0.0 | 0.0 | 0.0 | 0.0 | 0.0 | 122.4 |
| Light hydrocarbons | 0.0 | 0.0 | 0.0 | 0.0 | 0.0 | 115.6 |
| Benzene | 0.0 | 0.0 | 62.8 (100) | 0.0 | 0.0 | 36.1 (6.9) |
| Toluene | 0.0 | 537.4 (100) | 0.0 | 0.0 | 0.0 | 362.5 (21.6) |
| Ethylbenzene | 30.3 (3.6) | 0.0 | 0.0 | 0.0 | 0.0 | 29.9 (1.8) |
| Mixed xylenes | 814.5 (96.4) | 0.0 | 0.0 | 0.0 | 0.0 | 637.1 (38.0) |
| m-xylene | 469.0 (55.5) | — | — | — | — | 366.8 (21.9) |
| o-xylene | 183.1 (21.7) | — | — | — | — | 143.2 (8.5) |
| p-xylene | 162.4 (19.2) | — | — | — | — | 127.0 (7.6) |
| C9 aromatics total | 0.0 | 0.0 | 0.0 | 1003.2 (100) | 0.0 | 496.8 (29.6) |
| Trimethylbenzene | — | — | — | 998.7 (99.5) | — | 494.8 (29.5) |
| Methylethylbenzene | — | — | — | 4.5 (0.5) | — | 2.0 (0.1) |
| Propylbenzene | — | — | — | 0.0 (0.0) | — | 0.0 |
| C10+ aromatics | 0.0 | 0.0 | 0.0 | 0.0 | 83.1 (100) | 0.0 |

The production of mixed xylenes in Example 4 was 814.5 kg/hr. The overall conversion of trimethylbenzene and methylethylbenzene was 100%.

Example 5

Figure 7:
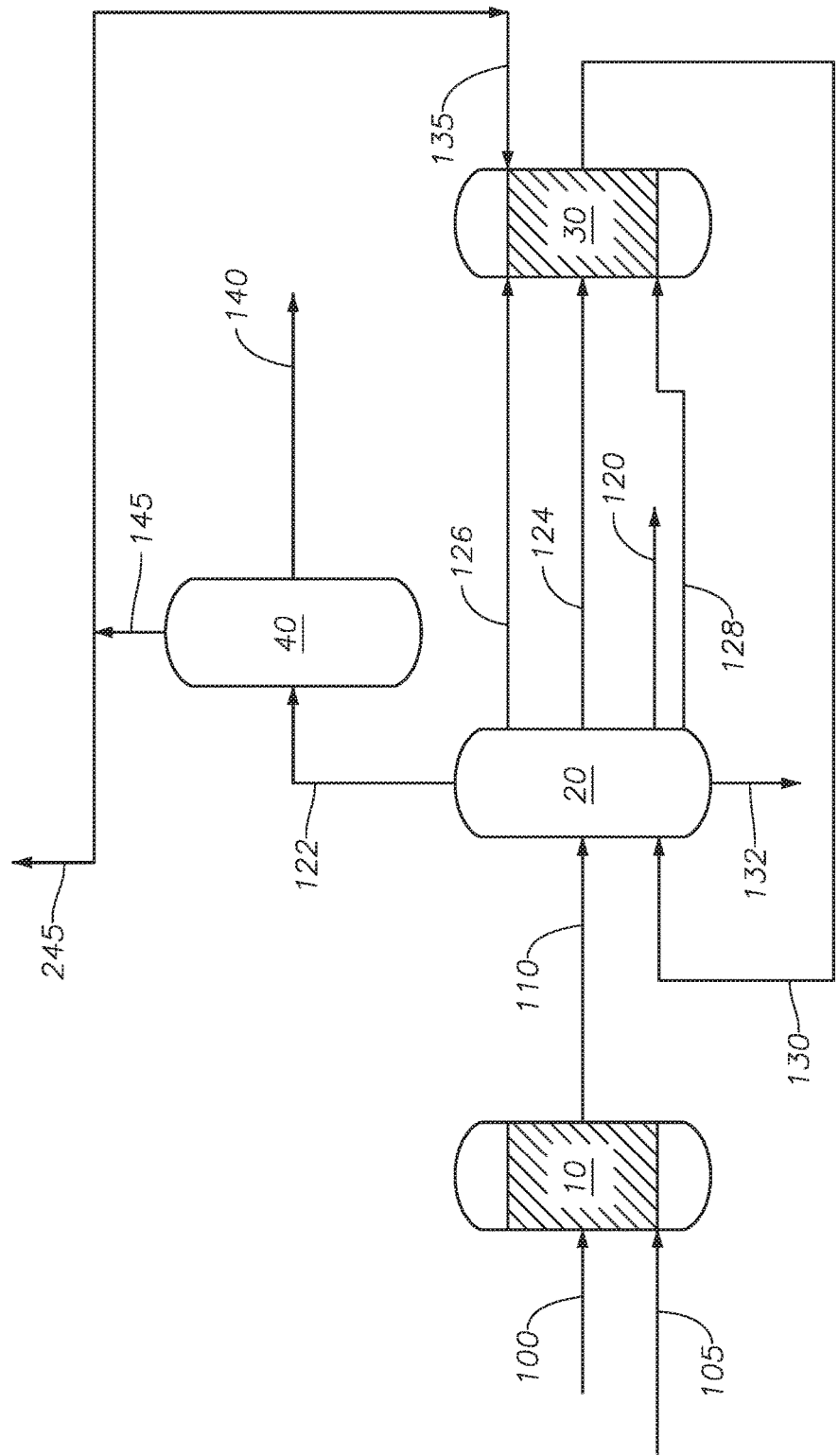
FIG. 7 provides a process diagram of an embodiment of the process.

Example 5 was a simulation of the process to produce mixed xylenes with reference to FIG. 7. Heavy reformate feed 100, having the composition in Table 11, was introduced to dealkylation reactor 10 along with hydrogen feed 105. The flow rate of hydrogen feed 105 was 138.6 kg/hr with 66.5 kg/hr hydrogen gas and 72.0 kg/hr light hydrocarbons.

TABLE 11

Composition of heavy reformate feed 100

| Component | Composition, kg/hr | Composition, wt % |
|---|---|---|
| Mass Flow | 1000.0 | 100 |
| Hydrogen | 0 | 0.0 |
| Light gases | 0 | 0.0 |
| Benzene | 0 | 0.0 |
| Toluene | 0 | 0.0 |
| Ethylbenzene | 0.5 | 0.0 |
| Mixed xylenes | 51.8 | 5.2 |
| m-xylene | 31.8 | 3.2 |

TABLE 11-continued

Composition of heavy reformate feed 100

| Component | Composition, kg/hr | Composition, wt % |
|---|---|---|
| o-xylene | 10.0 | 1.0 |
| p-xylene | 10.0 | 1.0 |
| C9 aromatics total | 801.6 | 80.2 |
| Trimethylbenzene | 565.5 | 56.5 |
| Methylethylbenzene | 210.9 | 21.1 |
| Propylbenzene | 25.2 | 2.5 |
| C10+ aromatics | 146.2 | 14.6 |

Dealkylation reactor 10 was at a temperature of 400 deg C. and a pressure of 30 bar (3000 kPa). The whsv was 4.2 hr$^{-1}$. The ratio of hydrogen gas (H$_2$) to hydrocarbons was 4:1 (mol/mol). The catalyst was a 3-dimensional zeolite-based dealkylation catalyst. The composition of dealkylation effluent 110 is shown in Table 12.

TABLE 12

Composition of dealkylation effluent 110

| Component | Composition, kg/hr | Composition, wt % calculated without hydrogen gas |
|---|---|---|
| Mass Flow | 1138.6 | — |
| Hydrogen | 63.0 | — |
| Light gases | 106.5 | 9.9 |
| Benzene | 26.8 | 2.5 |
| Toluene | 174.9 | 16.3 |
| Ethylbenzene | 0.4 | 0.0 |
| Mixed xylenes | 177.5 | 16.5 |
| m-xylene | 102.2 | 9.5 |

TABLE 12-continued

Composition of dealkylation effluent 110

| Component | Composition, kg/hr | Composition, wt % calculated without hydrogen gas |
|---|---|---|
| o-xylene | 39.9 | 3.7 |
| p-xylene | 35.4 | 3.3 |
| C9 aromatics total | 506.4 | 47.1 |
| Trimethylbenzene | 503.8 | 46.8 |
| Methylethylbenzene | 2.5 | 0.2 |
| Propylbenzene | 0.0 | 0.0 |
| C10+ aromatics | 83.1 | 7.7 |

Dealkylation effluent 110 was introduced to splitter unit 20 which separated dealkylation effluent 110 into its component parts. Light gas stream 122 was introduced to gas separator 40 to produce light gas product 140 and produced hydrogen 145. Produced hydrogen 145 was split to produce hydrogen slipstream 245 and hydrogen stream 135. The composition and flow rates are shown in Table 13.

TABLE 13

Composition of streams

| | Composition, kg/hr | | | | |
|---|---|---|---|---|---|
| Component | Stream 122 | Stream 140 | Stream 145 | Stream 135 | Stream 245 |
| Mass Flow | 388.0 | 216.0 | 172.0 | 113.6 | 58.4 |
| Hydrogen | 172.0 | 0.0 | 172.0 | 113.6 | 58.4 |
| Light gases | 216.0 | 216.0 | 0.0 | 0.0 | 0.0 |
| Benzene | 0.0 | 0.0 | 0.0 | 0.0 | 0.0 |
| Toluene | 0.0 | 0.0 | 0.0 | 0.0 | 0.0 |
| Ethylbenzene | 0.0 | 0.0 | 0.0 | 0.0 | 0.0 |
| Mixed xylenes | 0.0 | 0.0 | 0.0 | 0.0 | 0.0 |
| m-xylene | — | — | — | — | — |
| o-xylene | — | — | — | — | — |
| p-xylene | — | — | — | — | — |
| C9 aromatics total | 0.0 | 0.0 | 0.0 | 0.0 | 0.0 |
| Trimethylbenzene | — | — | — | — | — |
| Methylethylbenzene | — | — | — | — | — |
| Propylbenzene | — | — | — | — | — |
| C10+ aromatics | 0.0 | 0.0 | 0.0 | 0.0 | 0.0 |

Benzene stream 126, toluene stream 124, and C9 aromatics stream 128 were introduced to transalkylation reactor 30 with no surplus toluene. Hydrogen stream 135 was introduced to transalkylation reactor 30. Transalkylation reactor 30 was at a temperature of 400 deg C. and a pressure of 30 bar (3000 kPa). The whsv was 4.2 h$^{-1}$. The ratio of hydrogen gas (H$_2$) to hydrocarbons is 4:1 (mol/mol). The catalyst was a 1-dimensional zeolite-based transalkylation catalyst. The transalkylation catalyst was not the same as the dealkylation catalyst. The composition of various streams are shown in Table 14.

TABLE 14

Composition of Streams

| | Composition, kg/hr (wt % calculated with no hydrogen gas) | | | | | |
|---|---|---|---|---|---|---|
| Component | Stream 120 | Stream 124 | Stream 126 | Stream 128 | Stream 132 | Stream 130 |
| Mass Flow | 781.1 | 452.5 | 49.7 | 1026.2 | 83.1 | 1642.0 |
| Hydrogen | 0.0 | 0.0 | 0.0 | 0.0 | 0.0 | 109.0 |
| Light hydrocarbons | 0.0 | 0.0 | 0.0 | 0.0 | 0.0 | 109.4 (7.1) |
| Benzene | 0.0 | 0.0 | 49.7 (100) | 0.0 | 0.0 | 23.0 (1.5) |
| Toluene | 0.0 | 452.5 (100) | 0.0 | 0.0 | 0.0 | 277.6 (18.1) |
| Ethylbenzene | 25.4 (3.3) | 0.0 | 0.0 | 0.0 | 0.0 | 25.0 (1.6) |
| Mixed xylenes | 755.7 (96.7) | 0.0 | 0.0 | 0.0 | 0.0 | 578.2 (37.7) |
| m-xylene | 435.1 (55.7) | — | — | — | — | 332.9 (21.7) |

TABLE 14-continued

Composition of Streams

Composition, kg/hr (wt % calculated with no hydrogen gas)

| Component | Stream 120 | Stream 124 | Stream 126 | Stream 128 | Stream 132 | Stream 130 |
|---|---|---|---|---|---|---|
| o-xylene | 169.9 (21.8) | — | — | — | — | 130.0 (8.5) |
| p-xylene | 150.7 (19.3) | — | — | — | — | 115.3 (7.5) |
| C9 aromatics total | 0.0 | 0.0 | 0.0 | 1026.2 (100.0) | 0.0 | 519.8 (33.9) |
| Trimethylbenzene | — | — | — | 1021.7 (99.6) | — | 517.8 (33.8) |
| Methylethylbenzene | — | — | — | 4.5 (0.4) | — | 2.0 (0.1) |
| Propylbenzene | — | — | — | 0.0 | — | 0.0 |
| C10+ aromatics | 0.0 | 0.0 | 0.0 | 70.8 | 83.1 (100) | 0.0 (0) |

The production of mixed xylenes in Example 5 was 755.7 kg/hr. The conversion of trimethylbenzene in transalkylation reactor 30 was 51 wt %. The overall conversion of trimethylbenzene from heavy reformate feed 100 to mixed xylene stream 120 is 100 wt %. In other words, all trimethylbenzene in heavy reformate feed 100 is converted to xylenes in mixed xylene stream 120.

Comparing the production of mixed xylenes in Example 4 and Example 5 shows the increased yield due to the addition of surplus toluene to transalkylation reactor 30.

Example 6

Figure 8:
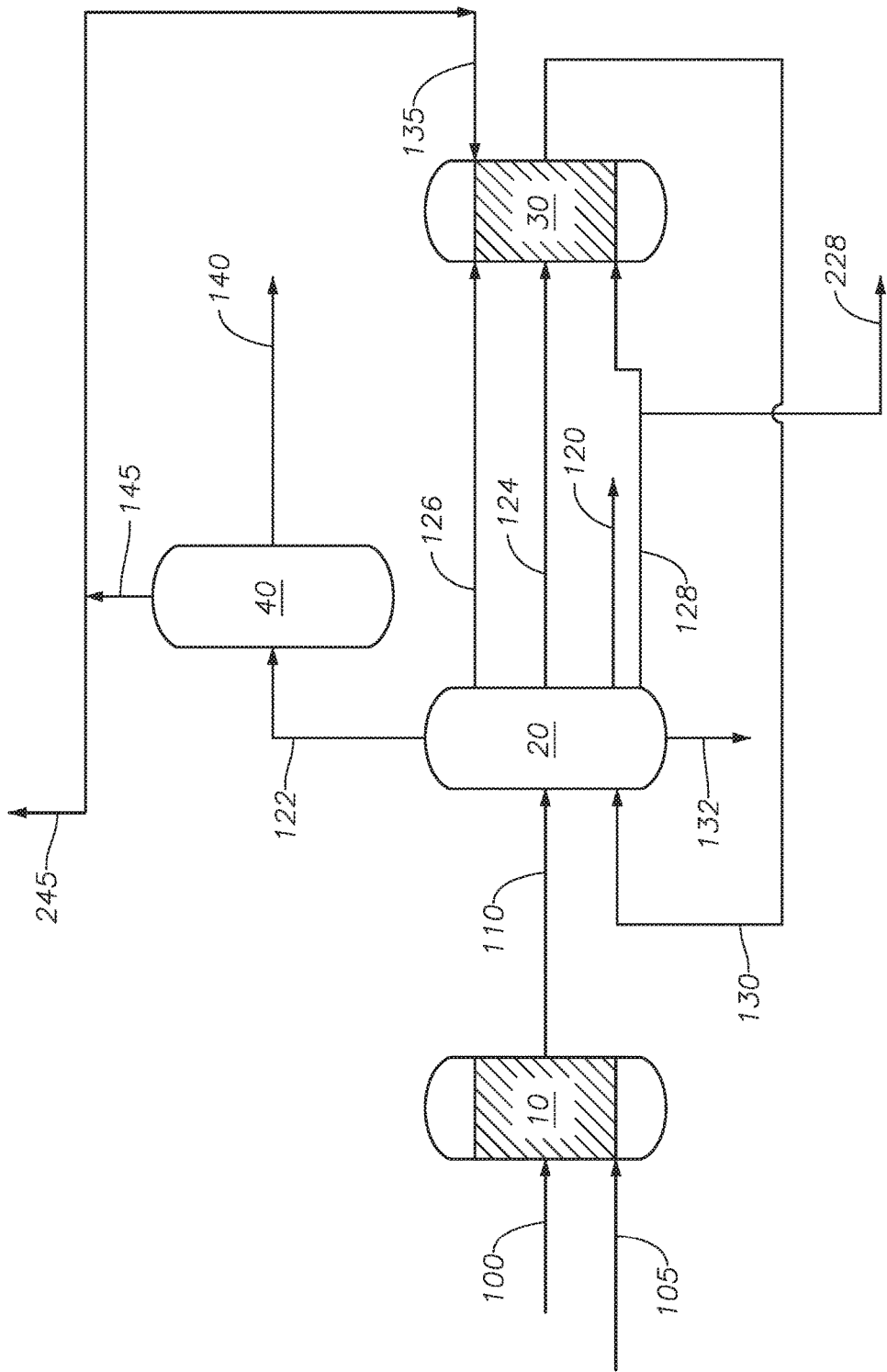
FIG. 8 provides a process diagram of an embodiment of the process.

Example 6 was a simulation of the process to produce mixed xylenes with reference to FIG. 8. Heavy reformate feed 100, having the composition in Table 15, was introduced to dealkylation reactor 10 along with hydrogen feed 105. The flow rate of hydrogen feed 105 was 138.6 kg/hr with 66.5 kg/hr hydrogen gas and 72.0 kg/hr light hydrocarbons.

TABLE 15

Composition of heavy reformate feed 100

| Component | Composition, kg/hr | Composition, wt % |
|---|---|---|
| Mass Flow | 1000.0 | 100 |
| Hydrogen | 0 | 0.0 |
| Light gases | 0 | 0.0 |
| Benzene | 0 | 0.0 |
| Toluene | 0 | 0.0 |
| Ethylbenzene | 0.5 | 0.0 |
| Mixed xylenes | 51.8 | 5.2 |
| m-xylene | 31.8 | 3.2 |
| o-xylene | 10.0 | 1.0 |
| p-xylene | 10.0 | 1.0 |
| C9 aromatics total | 801.6 | 80.2 |
| Trimethylbenzene | 565.5 | 56.5 |
| Methylethylbenzene | 210.9 | 21.1 |

TABLE 15-continued

Composition of heavy reformate feed 100

| Component | Composition, kg/hr | Composition, wt % |
|---|---|---|
| Propylbenzene | 25.2 | 2.5 |
| C10+ aromatics | 146.2 | 14.6 |

Dealkylation reactor 10 was at a temperature of 400 deg C. and a pressure of 30 bar (3000 kPa). The whsv was 4.2 hr$^{-1}$. The ratio of hydrogen gas ($H_2$) to hydrocarbons was 4:1 (mol/mol). The catalyst was a 3-dimensional zeolite-based dealkylation catalyst. The composition of dealkylation effluent 110 is shown in Table 16.

TABLE 16

Composition of dealkylation effluent 110

| Component | Composition, kg/hr | Composition, wt % calculated without hydrogen gas |
|---|---|---|
| Mass Flow | 1138.6 | — |
| Hydrogen | 63.0 | — |
| Light gases | 106.5 | 9.9 |
| Benzene | 26.8 | 2.5 |
| Toluene | 174.9 | 16.3 |
| Ethylbenzene | 0.4 | 0.0 |
| Mixed xylenes | 177.5 | 16.5 |
| m-xylene | 102.2 | 9.5 |
| o-xylene | 39.9 | 3.7 |
| p-xylene | 35.4 | 3.3 |
| C9 aromatics total | 506.4 | 47.1 |
| Trimethylbenzene | 503.8 | 46.8 |
| Methylethylbenzene | 2.5 | 0.2 |
| Propylbenzene | 0.0 | 0.0 |
| C10+ aromatics | 83.1 | 7.7 |

Dealkylation effluent 110 was introduced to splitter unit 20 which separated dealkylation effluent 110 into its component parts. Light gas stream 122 was introduced to gas separator 40 to produce light gas product 140 and produced hydrogen 145. Produced hydrogen 145 was split to produce hydrogen slipstream 245 and hydrogen stream 135. The composition and flow rates are shown in Table 17.

TABLE 17

Composition of streams

Composition, kg/hr

| Component | Stream 122 | Stream 140 | Stream 145 | Stream 135 | Stream 245 |
|---|---|---|---|---|---|
| Mass Flow | 361.7 | 207.7 | 154.0 | 94.3 | 59.7 |
| Hydrogen | 154.0 | 0.0 | 154.0 | 94.3 | 59.7 |
| Light gases | 207.7 | 207.7 | 0.0 | 0.0 | 0.0 |
| Benzene | 0.0 | 0.0 | 0.0 | 0.0 | 0.0 |

TABLE 17-continued

Composition of streams

| | Composition, kg/hr | | | | |
|---|---|---|---|---|---|
| Component | Stream 122 | Stream 140 | Stream 145 | Stream 135 | Stream 245 |
| Toluene | 0.0 | 0.0 | 0.0 | 0.0 | 0.0 |
| Ethylbenzene | 0.0 | 0.0 | 0.0 | 0.0 | 0.0 |
| Mixed xylenes | 0.0 | 0.0 | 0.0 | 0.0 | 0.0 |
| m-xylene | — | — | — | — | — |
| o-xylene | — | — | — | — | — |
| p-xylene | — | — | — | — | — |
| C9 aromatics total | 0.0 | 0.0 | 0.0 | 0.0 | 0.0 |
| Trimethylbenzene | — | — | — | — | — |
| Methylethylbenzene | — | — | — | — | — |
| Propylbenzene | — | — | — | — | — |
| C10+ aromatics | 0.0 | 0.0 | 0.0 | 0.0 | 0.0 |

Benzene stream 126 and toluene stream 124 were introduced to transalkylation reactor 30 with no surplus toluene. Hydrogen stream 135 was introduced to transalkylation reactor 30. C9 aromatics slip stream 228 was separated from C9 aromatics stream 128 with the remaining flow of C9 aromatics stream 128 introduced to transalkylation reactor 30. C9 aromatics slip stream 228 was adjusted to maintain a methyl to aromatic ring ratio of 2 in transalkylation reactor 30 in the absence of an added aromatic stream. Transalkylation reactor 30 was at a temperature of 400 deg C. and a pressure of 30 bar (3000 kPa). The whsv was 4.2 h$^{-1}$. The ratio of hydrogen gas (H$_2$) to hydrocarbons is 4:1 (mol/mol). The catalyst was a 1-dimensional zeolite-based transalkylation catalyst. The transalkylation catalyst was not the same as the dealkylation catalyst. The composition of various streams are shown in Table 18.

TABLE 18

Composition of Streams

| | Composition, kg/hr (wt % calculated with no hydrogen gas) | | | | | | |
|---|---|---|---|---|---|---|---|
| Component | Stream 120 | Stream 124 | Stream 126 | Stream 128 | Stream 228 | Stream 132 | Stream 130 |
| Mass Flow | 672.9 | 444.0 | 53.6 | 859.7 | 115.2 | 83.1 | 1336.3 |
| Hydrogen | 0.0 | 0.0 | 0.0 | 0.0 | 0.0 | 0.0 | 91.0 |
| Light hydrocarbons | 0.0 | 0.0 | 0.0 | 0.0 | 0.0 | 0.0 | 101.2 (8.1) |
| Benzene | 0.0 | 0.0 | 53.6 (100) | 0.0 | 0.0 | 0.0 | 26.8 (2.2) |
| Toluene | 0.0 | 444.0 (100) | 0.0 | 0.0 | 0.0 | 0.0 | 269.1 (21.6) |
| Ethylbenzene | 22.6 (3.4) | 0.0 | 0.0 | 0.0 | 0.0 | 0.0 | 22.2 (1.8) |
| Mixed xylenes | 650.3 (96.6) | 0.0 | 0.0 | 0.0 | 0.0 | 0.0 | 472.8 (38.0) |
| m-xylene | 374.4 (55.6) | — | — | — | — | — | 272.2 (21.9) |
| o-xylene | 146.2 (21.7) | — | — | — | — | — | 106.3 (8.5) |
| p-xylene | 129.7 (19.3) | — | — | — | — | — | 94.3 (7.6) |
| C9 aromatics total | 0.0 | 0.0 | 0.0 | 859.7 (100.0) | 115.2 (100.0) | 0.0 | 353.3 (28.4) |
| Trimethylbenzene | — | — | — | 855.6 (99.5) | 114.7 (99.6) | — | 351.8 (28.2) |
| Methylethylbenzene | — | — | — | 4.1 (0.5) | 0.5 (0.4) | — | 1.6 (0.1) |
| Propylbenzene | — | — | — | 0.0 | 0.0 | — | 0.0 |
| C10+ aromatics | 0.0 | 0.0 | 0.0 | 70.8 | 0.0 | 83.1 (100) | 0.0 (0) |

The production of mixed xylenes in Example 6 was 650.3 kg/hr. The overall conversion of trimethylbenzene is 80 wt %.

Comparing the production rate of mixed xylenes in Example 5 and Example 6 shows that introducing the entire flow rate of the C9 aromatics stream into the transalkylation reactor increases production of mixed xylenes.

Example 7

Figure 9:
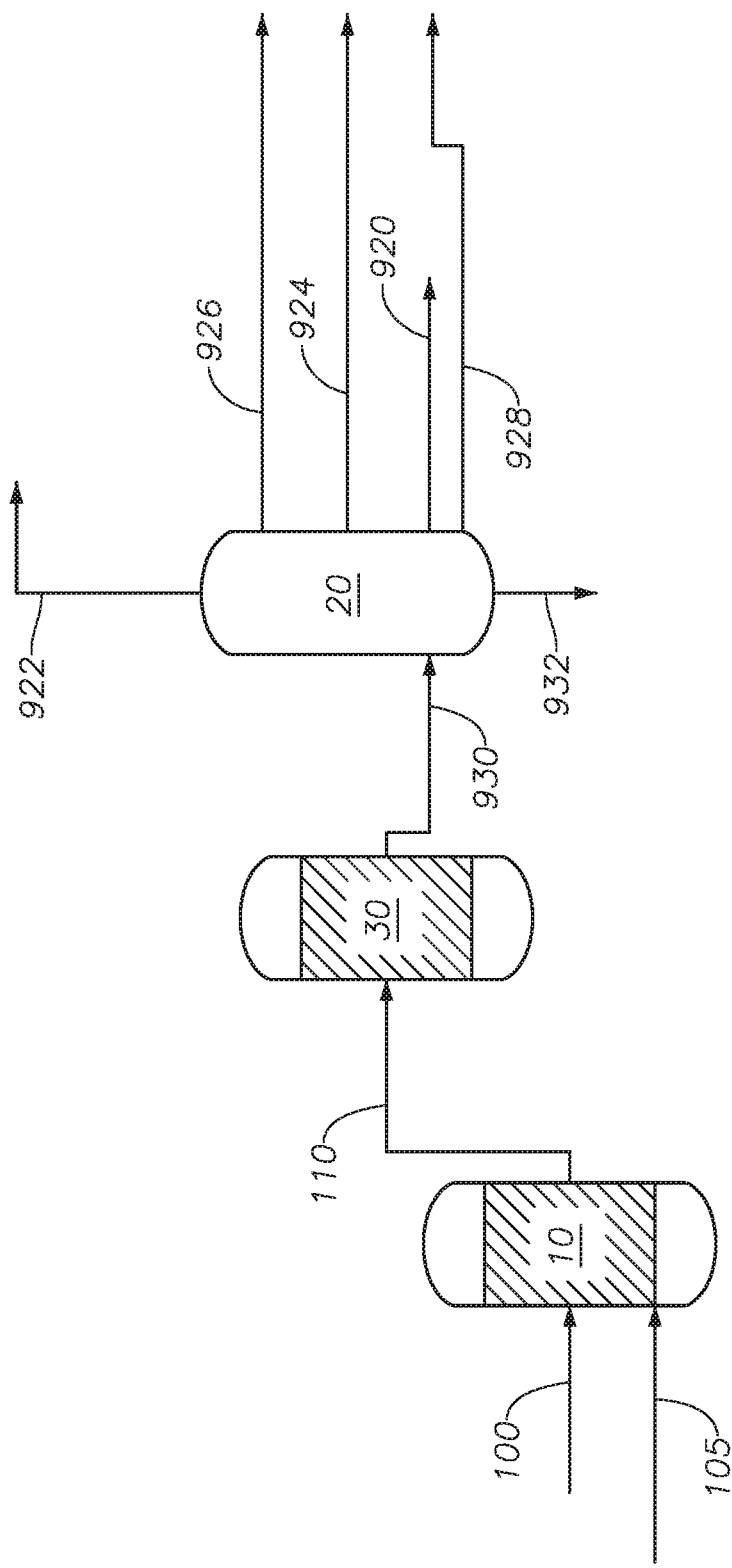
FIG. 9 provides a process diagram of a process in the absence of a splitter unit between a dealkylation reactor and transalkylation reactor.

Example 7 was a comparative example in the absence of a splitter unit between the dealkylation reactor and transalkylation reactor with reference to FIG. 9. Heavy reformate feed 100, having the composition in Table 19, was introduced to dealkylation reactor 10 along with hydrogen feed 105. The flow rate of hydrogen feed 105 was 138.6 kg/hr with 66.5 kg/hr hydrogen gas and 72.0 kg/hr light hydrocarbons.

TABLE 19

Composition of heavy reformate feed 100

| Component | Composition, kg/hr | Composition, wt % |
|---|---|---|
| Mass Flow | 1000.0 | 100 |
| Hydrogen | 0 | 0.0 |
| Light gases | 0 | 0.0 |
| Benzene | 0 | 0.0 |

TABLE 19-continued

Composition of heavy reformate feed 100

| Component | Composition, kg/hr | Composition, wt % |
|---|---|---|
| Toluene | 0 | 0.0 |
| Ethylbenzene | 0.5 | 0.0 |
| Mixed xylenes | 51.8 | 5.2 |
| m-xylene | 31.8 | 3.2 |
| o-xylene | 10.0 | 1.0 |
| p-xylene | 10.0 | 1.0 |
| C9 aromatics total | 801.6 | 80.2 |

TABLE 19-continued

Composition of heavy reformate feed 100

| Component | Composition, kg/hr | Composition, wt % |
|---|---|---|
| Trimethylbenzene | 565.5 | 56.5 |
| Methylethylbenzene | 210.9 | 21.1 |
| Propylbenzene | 25.2 | 2.5 |
| C10+ aromatics | 146.2 | 14.6 |

Dealkylation reactor 10 was at a temperature of 400 deg C. and a pressure of 30 bar (3000 kPa). The whsv was 4.2 $hr^{-1}$. The ratio of hydrogen gas ($H_2$) to hydrocarbons was 4:1 (mol/mol). The catalyst was a 3-dimensional zeolite-based dealkylation catalyst. The composition of dealkylation effluent 110 is shown in Table 20.

TABLE 20

Composition of dealkylation effluent 110

| Component | Composition, kg/hr | Composition, wt % calculated without hydrogen gas |
|---|---|---|
| Mass Flow | 1138.6 | — |
| Hydrogen | 63.0 | — |
| Light gases | 106.5 | 9.9 |
| Benzene | 26.8 | 2.5 |
| Toluene | 174.9 | 16.3 |
| Ethylbenzene | 0.4 | 0.0 |
| Mixed xylenes | 177.5 | 16.5 |
| m-xylene | 102.2 | 9.5 |
| o-xylene | 39.9 | 3.7 |
| p-xylene | 35.4 | 3.3 |
| C9 aromatics total | 506.4 | 47.1 |
| Trimethylbenzene | 503.8 | 46.8 |
| Methylethylbenzene | 2.5 | 0.2 |
| Propylbenzene | 0.0 | 0.0 |
| C10+ aromatics | 83.1 | 7.7 |

Dealkylation effluent 110 was introduced to transalkylation reactor 30. Transalkylation reactor 30 was at a temperature of 400 deg C. and a pressure of 30 bar (3000 kPa). The whsv was 4.2 $h^{-1}$. The ratio of hydrogen gas ($H_2$) to hydrocarbons is 4:1 (mol/mol). The catalyst was a 1-dimensional zeolite-based transalkylation catalyst. The transalkylation catalyst was not the same as the dealkylation catalyst. Transalkylation product 930 was introduced to splitter unit 20 which separated transalkylation product 930 into its component parts: mixed xylenes fraction 920, light gases fraction 922, toluene fraction 924, benzene fraction 926, C9 aromatics fraction 928, and C10+ aromatics fraction 932. The composition of various streams are shown in Table 21.

TABLE 21

Composition of Streams

Composition, kg/hr (wt % calculated without hydrogen gas)

| Component | Stream 930 | Stream 920 | Stream 922 | Stream 924 | Stream 926 | Stream 928 | Stream 932 |
|---|---|---|---|---|---|---|---|
| Mass Flow | 1138.6 | 425.9 | 155.5 | 308.1 | 42.1 | 161.3 | 45.7 |
| Hydrogen | 60.8 | 0.0 | 60.8 | 0.0 | 0.0 | 0.0 | 0.0 |
| Light hydrocarbons | 94.7 (8.8) | 0.0 | 94.7 (100) | 0.0 | 0.0 | 0.0 | 0.0 |
| Benzene | 42.1 (3.9) | 0.0 | 0.0 | 0.0 | 42.1 (100) | 0.0 | 0.0 |
| Toluene | 308.1 (28.6) | 0.0 | 0.0 | 308.1 (100) | 0.0 | 0.0 | 0.0 |
| Ethylbenzene | 20.1 (1.9) | 20.1 (4.7) | 0.0 | 0.0 | 0.0 | 0.0 | 0.0 |
| Mixed xylenes | 405.8 (37.6) | 405.8 (95.3) | 0.0 | 0.0 | 0.0 | 0.0 | 0.0 |
| m-xylene | 233.6 (21.7) | 233.6 (54.9) | — | — | — | — | — |
| o-xylene | 91.2 (8.5) | 91.2 (21.4) | — | — | — | — | — |
| p-xylene | 80.9 (7.5) | 80.9 (19.0) | — | — | — | — | — |
| C9 aromatics total | 161.3 (15.0) | 0.0 | 0.0 | 0.0 | 0.0 | 161.3 (100.0) | 0.0 |
| Trimethylbenzene | 160.2 (14.9) | — | — | — | — | 160.2 (99.3) | — |
| Methylethylbenzene | 1.1 (0.1) | — | — | — | — | 1.1 (0.7) | — |
| Propylbenzene | 0.0 | — | — | — | — | 0.0 | — |
| C10+ aromatics | 45.7 (4.2) | 0.0 | 0.0 | 0.0 | 0.0 | 0.0 | 45.7 (100) |

The production of mixed xylenes was 405.8 kg/hr. The overall conversion of trimethylbenzene is 72 wt %.

Comparing the production rate of mixed xylenes in Example 4 and Example 7 shows that the addition of a splitter unit and the associated process stream configuration changes unexpectedly and advantageously increases the production rate of mixed xylenes by about 100%.

Although the embodiments have been described in detail, it should be understood that various changes, substitutions, and alterations can be made without departing from the principle and scope. Accordingly, the scope of the present embodiments should be determined by the following claims and their appropriate legal equivalents.

There various elements described can be used in combination with all other elements described here unless otherwise indicated.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed here as from about one particular value to about another particular value and are inclusive unless otherwise indicated. When such a range is expressed, it is to be understood that another embodiment is from the one particular value to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made here.

As used here and in the appended claims, the words "comprise," "has," and "include" and all grammatical variations thereof are each intended to have an open, non-limiting meaning that does not exclude additional elements or steps.

That which is claimed is:

1. A method for producing mixed xylenes from a heavy reformate feed, the method comprising the steps of:
    introducing the heavy reformate feed and a hydrogen feed to a dealkylation reactor, wherein the dealkylation reactor comprises a dealkylation catalyst, wherein the heavy reformate comprises toluene and aromatic hydrocarbons with nine or more carbon atoms (C9+ aromatics), wherein the hydrogen feed comprises hydrogen gas;
    reacting the heavy reformate feed with the hydrogen gas in the presence of the dealkylation catalyst in the dealkylation reactor to produce a dealkylation effluent, wherein the dealkylation reactor is at a dealkylation temperature, wherein the dealkylation reactor is at a dealkylation pressure, wherein the dealkylation reactor has a liquid hourly space velocity;
    introducing the dealkylation effluent to a splitter unit, where the dealkylation effluent comprises light gases, toluene, benzene, mixed xylenes, and C9+ aromatics;
    separating the dealkylation effluent into a light gas stream, a toluene stream, a benzene stream, a C9 aromatics stream, a C10+ aromatics stream, and a mixed xylene stream in the splitter unit, wherein the light gas stream comprises light hydrocarbons and hydrogen, wherein the toluene stream comprises toluene, wherein the benzene stream comprises benzene, wherein the mixed xylene stream comprises mixed xylenes, wherein the C9 stream comprises C9 aromatics, wherein the C10+ aromatics stream comprises C10+ aromatics;
    introducing the toluene stream, the C9 aromatics stream, and a hydrogen stream into a transalkylation reactor, wherein the transalkylation reactor comprises a transalkylation catalyst, wherein the hydrogen stream comprises hydrogen gas;
    reacting the toluene stream and the C9 aromatics stream in the presence of the transalkylation catalyst to produce a transalkylation effluent, wherein the transalkylation reactor is at a transalkylation temperature, wherein the transalkylation reactor is at a transalkylation pressure, wherein the transalkylation reactor has a liquid hourly space velocity;
    introducing the transalkylation effluent to the splitter unit, wherein the transalkylation effluent comprises light gases, toluene, benzene, mixed xylenes, and C9+ aromatics; and
    separating the transalkylation effluent in the splitter unit such that mixed xylenes in the transalkylation effluent exit the splitter unit as part of the mixed xylene stream.

2. The method of claim 1, wherein the heavy reformate feed contains between 0 wt % and 60 wt % toluene.

3. The method of claim 1 further comprising the steps of:
    introducing the light gas stream to a gas separator; and
    separating the light gas stream into a produced hydrogen and a light gas product.

4. The method of claim 3, where the gas separator comprises a pressure swing adsorption unit.

5. The method of claim 1 further comprising the step of introducing the benzene stream to the transalkylation reactor.

6. The method of claim 1 further comprising the step of supplying an added aromatic stream to the transalkylation reactor, such that there is an excess of toluene for transalkylation reactions in the transalkylation reactor.

7. The method of claim 1, wherein the dealkylation temperature is between 200 deg C. and 500 deg C.

8. The method of claim 1, wherein the dealkylation pressure is between 5 bar and 40 bar.

9. The method of claim 1, wherein the liquid hourly space velocity in the dealkylation reactor is between 1 hr-1 and 10 hr-1.

10. The method of claim 1, wherein the transalkylation temperature is between 300 deg C. and 500 deg C.

11. The method of claim 1, wherein the transalkylation pressure is between 10 bar and 40 bar.

12. The method of claim 1, wherein the liquid hourly space velocity in the transalkylation reactor is between 0.5 hr-1 and 6 hr-1.

13. The method of claim 1, wherein an overall yield of the mixed xylenes in the mixed xylene stream is between 30 wt % and 89 wt %.

14. A method for producing mixed xylenes from a heavy reformate feed, the method comprising the steps of:
    introducing the heavy reformate feed and a hydrogen feed to a dealkylation reactor, wherein the dealkylation reactor comprises a dealkylation catalyst, wherein the heavy reformate comprises aromatic hydrocarbons with nine or more carbon atoms (C9+ aromatics), wherein the hydrogen feed comprises hydrogen gas;
    reacting the heavy reformate feed with the hydrogen gas in the presence of the dealkylation catalyst in the dealkylation reactor to produce a dealkylation effluent, wherein the dealkylation reactor is at a dealkylation temperature, wherein the dealkylation reactor is at a dealkylation pressure, wherein the dealkylation reactor has a liquid hourly space velocity;
    introducing the dealkylation effluent to a splitter unit, where the dealkylation effluent comprises light gases, toluene, benzene, mixed xylenes, and C9+ aromatics, where the splitter unit comprises multiple splitter columns;
    separating the dealkylation effluent into a light gas stream, a toluene stream, a benzene stream, a C9 aromatics stream, a C10+ aromatics stream, and a mixed xylene stream in the splitter unit, wherein the light gas stream comprises light hydrocarbons and hydrogen, wherein the toluene stream comprises toluene, wherein the benzene stream comprises benzene, wherein the mixed xylene stream comprises mixed xylenes, wherein the C9 stream comprises C9 aromatics, wherein the C10+ aromatics stream comprises C10+ aromatics;
    introducing the toluene stream, the C9 aromatics stream, and a hydrogen stream into a transalkylation reactor, wherein the transalkylation reactor comprises a transalkylation catalyst, wherein the hydrogen stream comprises hydrogen gas;
    reacting the toluene stream and the C9 aromatics stream in the presence of the transalkylation catalyst to produce a transalkylation effluent, wherein the transalkylation reactor is at a transalkylation temperature, wherein the transalkylation reactor is at a transalkylation pressure, wherein the transalkylation reactor has a liquid hourly space velocity;
    introducing the transalkylation effluent to the splitter unit, wherein the transalkylation effluent comprises light gases, toluene, benzene, mixed xylenes, and C9+ aromatics; and separating the transalkylation effluent in the splitter unit such that mixed xylenes in the transalkylation effluent exit the splitter unit as part of the mixed xylene stream.

15. The method of claim 14 further comprising the steps of:
introducing the light gas stream to a gas separator; and
separating the light gas stream into a produced hydrogen and a light gas product.

16. The method of claim 15, where the gas separator comprises a pressure swing adsorption unit.

17. The method of claim 14 further comprising the step of introducing the benzene stream to the transalkylation reactor.

18. The method of claim 14 further comprising the step of supplying an added aromatic stream to the transalkylation reactor, such that there is an excess of toluene for transalkylation reactions in the transalkylation reactor.

19. The method of claim 14, wherein the dealkylation temperature is between 200 deg C. and 500 deg C.

20. The method of claim 14, wherein the dealkylation pressure is between 5 bar and 40 bar.

21. The method of claim 14, wherein the liquid hourly space velocity in the dealkylation reactor is between 1 hr-1 and 10 hr-1.

22. The method of claim 14, where the step of separating the dealkylation effluent comprises the steps of:
introducing the dealkylation effluent into a first column;
separating the dealkylation effluent in the first column to produce the light gas stream and a first column effluent;
introducing the first column effluent into a second column;
separating the first column effluent in the second column to produce a benzene/toluene stream and a second column effluent;
introducing the benzene/toluene stream into a third column;
separating the benzene/toluene stream in a third column to produce the benzene stream and the toluene stream;
introducing second column effluent into a fourth column;
separating the second column effluent in the fourth column to produce the mixed xylene stream and a C9+ aromatics stream;
introducing the C9+ aromatics stream into a fifth column; and
separating the C9+ aromatics stream in the fifth column to produce the C9 aromatics stream and the C10+ aromatics stream.

23. The method of claim 14, wherein the transalkylation temperature is between 300 deg C. and 500 deg C.

24. The method of claim 14, wherein the transalkylation pressure is between 10 bar and 40 bar.

25. The method of claim 14, wherein the liquid hourly space velocity in the transalkylation reactor is between 0.5 hr-1 and 6 hr-1.

26. The method of claim 14, wherein an overall yield of the mixed xylenes in the mixed xylene stream is between 30 wt % and 89 wt %.

* * * * *